United States Patent
Seal et al.

(10) Patent No.: US 8,012,981 B2
(45) Date of Patent: Sep. 6, 2011

(54) BENZYLPIPERAZINE DERIVATIVES AS MOTILIN RECEPTOR AGONISTS

(75) Inventors: Jonathan Thomas Seal, Harlow (GB); Geoffrey Stemp, Harlow (GB); Mervyn Thompson, Harlow (GB); Susan Marie Westaway, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/304,539

(22) PCT Filed: Jun. 14, 2007

(86) PCT No.: PCT/EP2007/055890
§ 371 (c)(1),
(2), (4) Date: Dec. 12, 2008

(87) PCT Pub. No.: WO2007/144400
PCT Pub. Date: Dec. 21, 2007

(65) Prior Publication Data
US 2009/0131453 A1    May 21, 2009

(30) Foreign Application Priority Data
Jun. 15, 2006    (GB) .................... 0611907.7

(51) Int. Cl.
*A61K 31/496*    (2006.01)
*C07D 401/12*    (2006.01)
*C07D 401/14*    (2006.01)
(52) U.S. Cl. .................... 514/253.13; 544/360; 544/364
(58) Field of Classification Search .................... None
See application file for complete search history.

(56) References Cited

U.S. PATENT DOCUMENTS

| | | | |
|---|---|---|---|
| 5,385,912 A | 1/1995 | Neuenschwander et al. | 514/305 |
| 5,494,918 A | 2/1996 | Neuenschwander et al. | 514/305 |
| 5,593,994 A | 1/1997 | Batt et al. | 514/252 |
| 5,912,235 A | 6/1999 | Hoeltje et al. | 514/28 |
| 5,932,586 A | 8/1999 | Batt et al. | 514/277 |
| 5,965,578 A | 10/1999 | Graham et al. | 514/326 |
| 5,972,939 A | 10/1999 | Chen et al. | 514/237.8 |
| 6,100,239 A | 8/2000 | Ataka et al. | 514/28 |
| 6,165,985 A | 12/2000 | Jasserand et al. | 514/28 |
| 6,200,978 B1 | 3/2001 | Maw et al. | 514/254.05 |
| 6,384,031 B2 | 5/2002 | Chen et al. | 514/237.8 |
| 6,392,040 B2 | 5/2002 | Chen et al. | 544/134 |
| 6,426,346 B1 | 7/2002 | Pruitt et al. | 514/249 |
| 6,624,165 B2 | 9/2003 | Chen et al. | 514/236.2 |
| 6,667,309 B2 | 12/2003 | Chen et al. | 514/237.8 |
| 6,977,264 B2 | 12/2005 | Fotsch et al. | 514/330 |
| 7,223,788 B2 | 5/2007 | Schwink et al. | 514/426 |
| 7,262,195 B2 | 8/2007 | Li et al. | 514/252.06 |
| 7,700,599 B2 | 4/2010 | Thompson et al. | 514/253.12 |
| 7,767,692 B2 * | 8/2010 | Jasserand et al. | 514/315 |
| 2002/0010184 A1 | 1/2002 | Dinsmore et al. | 514/253.09 |
| 2002/0052380 A1 | 5/2002 | Dinsmore et al. | 514/254.05 |
| 2003/0203922 A1 | 10/2003 | Patel et al. | 514/266.21 |
| 2004/0152732 A1 | 8/2004 | Jasserand et al. | 514/317 |
| 2005/0065156 A1 | 3/2005 | Lit et al. | 514/248 |
| 2005/0080116 A1 | 4/2005 | Li et al. | 514/364 |
| 2005/0272722 A1 | 12/2005 | Lansbury et al. | 514/221 |
| 2005/0277629 A1 | 12/2005 | Lansbury et al. | 514/218 |
| 2005/0288298 A1 | 12/2005 | Lansbury et al. | 514/253.03 |
| 2006/0106060 A1 | 5/2006 | Lansbury et al. | 514/312 |
| 2007/0225292 A1 | 9/2007 | Amin et al. | 514/252.1 |
| 2007/0293539 A1 | 12/2007 | Lansbury et al. | 514/319 |
| 2008/0027065 A1 | 1/2008 | Mitchell et al. | 514/252.11 |
| 2008/0306083 A1 | 12/2008 | MacDonald et al. | 514/253.1 |
| 2009/0054456 A1 | 2/2009 | Johnson et al. | 514/253.13 |
| 2009/0192160 A1 | 7/2009 | Mitchell et al. | 514/235.8 |
| 2010/0256364 A1 | 10/2010 | Mitchell et al. | 544/121 |

FOREIGN PATENT DOCUMENTS

| | | |
|---|---|---|
| DE | 19805822 B4 | 2/1998 |
| EP | 838469 | 10/1997 |
| JP | 1994211886 A | 8/1994 |
| JP | 09249620 | 9/1997 |
| WO | WO 92/15579 A1 | 9/1992 |
| WO | WO 94/10185 | 5/1994 |
| WO | WO 96/10012 A1 | 4/1996 |
| WO | WO 97/36605 A1 | 10/1997 |
| WO | WO 98/23629 A1 | 6/1998 |
| WO | WO 99/21846 A1 | 5/1999 |
| WO | WO 01/60368 A1 | 8/2001 |

(Continued)

OTHER PUBLICATIONS

Ozaki et al. Pharmacology, vol. 79, p. 223-235 (2007).*
ter Beek et al. Inflamm. Bowel Dis. vol. 14,p. 612-619 (2008).*
Suzuki et al. Chemical Abstracts, vol. 127, No. 60085a (1997), Abstract for JP 09249620 (Sep. 22, 1997).*
International Search Report dated Oct. 19, 2007, PCT/EP2007/055890.
*Chemical Abstracts Service*, Caplus, XP002452868, 2005: 61224, Asaki et al. (2005).

(Continued)

*Primary Examiner* — Emily Bernhardt
(74) *Attorney, Agent, or Firm* — Kathryn L. Sieburth; John Lemanowicz

(57) ABSTRACT

The invention relates to compounds of formula (I):

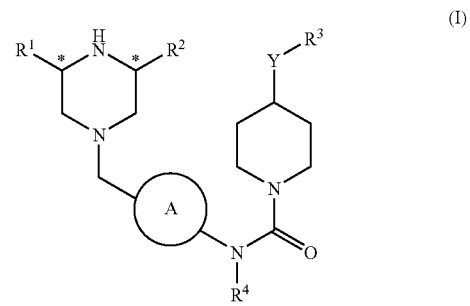

processes for their preparation, pharmaceutical compositions containing them and their use in the treatment of conditions or disorders which are mediated via the GPR38 receptor.

22 Claims, No Drawings

FOREIGN PATENT DOCUMENTS

| | | |
|---|---|---|
| WO | WO 01/60815 A1 | 8/2001 |
| WO | WO 01/68620 A1 | 9/2001 |
| WO | WO 01/68622 A1 | 9/2001 |
| WO | WO 01/85694 A | 11/2001 |
| WO | WO 02/092592 A | 11/2002 |
| WO | WO 03/009847 A1 | 2/2003 |
| WO | WO 2004/037257 A | 5/2004 |
| WO | WO 01/68621 A | 9/2004 |
| WO | WO 2005/027637 A1 | 3/2005 |
| WO | WO 2005/063720 A1 | 7/2005 |
| WO | WO 2005/077345 A1 | 8/2005 |
| WO | WO 2005/077368 A2 | 8/2005 |
| WO | WO 2005/077373 A2 | 8/2005 |
| WO | WO 2005/089502 A2 | 9/2005 |
| WO | WO 2005/115986 A1 | 12/2005 |
| WO | WO 2006/014135 A | 2/2006 |
| WO | WO 2007/007018 A1 | 1/2007 |
| WO | WO 2007/012479 A | 2/2007 |
| WO | WO 2008/000729 A1 | 1/2008 |

OTHER PUBLICATIONS

English translation for JP 09249620 (Sep. 1997).
Filewrapper for U.S. Appl. No. 11/995,416 filed Jun. 9, 2008.
Filewrapper for U.S. Appl. No. 12/096,104 filed Jun. 4, 2008.
Filewrapper for U.S. Appl. No. 11/768,339 filed Jun. 26, 2007.
Filewrapper for U.S. Appl. No. 12/417,176 filed Apr. 2, 2009.
Filewrapper for U.S. Appl. No. 12/744,367 filed May 24, 2010.
Li, et al. "Discovery of a Potent and Novel Moitlin Agonist", *J. Med. Chem.*, 47(7): 1704-1708 (2004).

* cited by examiner

BENZYLPIPERAZINE DERIVATIVES AS MOTILIN RECEPTOR AGONISTS

This application is a 371 of International Application No. PCT/EP2007/055890, filed 14 Jun. 2007, which claims the priority of GB Application No. 0611907.7, filed Jun. 15, 2006, which is incorporated herein in its entirety.

The present invention relates to novel benzylpiperazine derivatives having pharmacological activity, processes for their preparation, pharmaceutical compositions containing them and their use in the treatment of various disorders.

GPR38 is a 7-transmembrane, G-protein coupled receptor, with high affinity for the peptide motilin [Feighner et al., *Science* 1999, 284, 2184], suggesting that endogenous motilin exerts all or most of its activity via this receptor.

Motilin is a 22 amino acid peptide found in large amounts within endocrine-like cells of the gastrointestinal tract, and especially in the duodenum-jejunum areas. During fasting, the peptide is known to be associated with the onset of Phase III migrating complex activity within the stomach [Boivin et al., *Dig. Dis. Sci.* 1992, 37, 1562], suggesting a role in the mechanisms of prokinetic activity. Motilin is also released from the gut during feeding, sham feeding, gastric distension or by oral or intravenous nutrient application [Christofides et al., *Gut* 1979, 20, 102; Bormans et al., *Scand. J. Gastroenterol.* 1987, 22, 781], suggesting additional roles for this peptide in the modulation of motility patterns during feeding.

In animals or in man, motilin has long been known to increase gastrointestinal motility, and promote gastric emptying and intestinal propulsion in an anal direction, during both fasting and fed conditions. This activity is thought to be primarily due to a facilitation of at least the cholinergic excitatory function of the gut [Van Assche et al., *Eur. J. Pharmacol.* 1997, 337, 267], perhaps also involving the activation of the vagus nerve [Mathis & Malbert, *Am. J. Physiol.* 1998, 274, G80]. In addition, higher concentrations of motilin directly evoke a small contraction of the muscle [Van Assche et al., *Eur. J. Pharmacol.* 1997, 337, 267].

The antibiotic erythromycin was shown to mimic the gastrointestinal activity of motilin, in addition to its previously-described antibiotic properties [see Peeters, in *Problems of the Gastrointestinal Tract in Anaesthesia* Ed., Herbert M K et al. Springer-Verlag, Berlin, Heidelberg 1999, pp 39-51]. More recently, erythromycin has been shown to activate the GPR38 receptor, confirming its ability to mimic the function of motilin [Carreras et al., *Analyt. Biochem.* 2002, 300, 146]. In addition, the availability of this non-peptide motilin receptor agonist has allowed at least some clinical studies to be undertaken in order to examine the clinical potential of motilin receptor agonists. These studies have consistently demonstrated an ability to increase gastric emptying in various conditions associated with gastroparesis, such as functional dyspepsia and diabetic gastroparesis. Further, erythromycin has been shown to increase lower esophageal sphincter pressure in man, which together with the increase in gastric emptying, suggests a role in the treatment of gastroesophageal reflux disorders (GERD). Finally, erythromycin has been used to promote intestinal propulsive activity, finding clinical utility in the treatment of pseudo-obstruction and in conditions with impaired colonic motility [Peeters, in *Problems of the Gastrointestinal Tract in Anaesthesia* Ed., Herbert M K et al. Springer-Verlag, Berlin, Heidelberg 1999, pp 39-51].

Consequently it is expected that agonists at the GPR38 receptor will mimic the activity of motilin or of other substances acting at this receptor, such as erythromycin, and find clinical utility in the treatment of gastrointestinal disorders associated with hypomotility, especially the functional bowel disorders such as GERD, functional dyspepsia (FD) and irritable bowel syndrome (IBS). The compounds will also be useful for the treatment of other GI conditions where the cause is known and in which GI motility is reduced. Such conditions include constipation, caused by various diseases such as those associated with neuropathy, and/or by the administration of other drugs, intestinal pseudo-obstruction, paralytic ileus following surgery or some other manipulation, gastric stasis or hypomotility caused by various diseases such as diabetes and/or by the administration of other drugs or in enterally fed patients. Interestingly, the ability of motilin or erythromycin to activate the vagus nerve, the association of this nerve with changes in feeding behaviour [e.g. Furness et al., *Auton. Neurosci.* 2001, 92, 28] and the chromosomal location of GPR38 [based on Ensembl: 13q21.1 (58.46-59.46 Mb)] within the markers (D13S257-13q14.11 to D13S258 at 13q21.33) of a locus associated with obesity [Feitosa et al, *Am. J. Hum. Genet.* 2002, 70, 72] also suggests that agonists active at the GPR38 receptor will, in addition to promoting gastrointestinal motility, facilitate eating behaviours in at least those patients in which some degree of appetite suppression or cachexia is present. Such activity indicates that agonists at this receptor will find clinical utility in the treatment of symptoms associated with—for example—the treatment of cancer or by the presence of the cancer itself.

In addition to the ability of motilin receptor agonists to promote gastrointestinal motility, the association of motilin gene polymorphism with Crohn's disease [Annese et al., *Dig. Dis. Sci.* 1998, 43, 715-710] and the changes in motilin receptor density during colitis [Depoortere et al., *Neurogastroenterol. Motil.* 2001, 13, 55] suggests a utility for agonists at the motilin receptor for the treatment of inflammatory bowel conditions in general.

Finally, GPR38 is also found in regions outside the gastrointestinal tract. These areas include the pituitary, adipose tissue, urinary bladder and certain areas of the brain. The former suggests clinical utility in the promotion of pituitary function, such as the release of growth hormone secretagogues, the presence within adipose tissue again suggests a role in the control of body weight, and the presence within the urinary bladder suggests a role for agonists at this receptor in the treatment of incontinence. The presence of GPR38 within the brain supports the gastrointestinal and feeding utilities already mentioned, but in addition, suggests an involvement of the receptor in a greater spectrum of vagal-hypothalamic functions.

WO9410185, EP838469, WO9823629, DE19805822, and U.S. Pat. No. 6,165,985 claim erythromycin derivatives targeting GPR38 for use in disorders relating to gastrointestinal motility. WO9921846, WO0185694, WO0168620, WO0168621, and WO0168622 disclose a series of small molecule antagonists of the GPR38 receptor. JP07138284 and EP807639 disclose peptide agonists. JP09249620, WO02092592, WO05027637, US2005065156 and Li et al., (2004, Journal of Medicinal Chemistry, 47 (7) p 1704-1708) disclose series of small molecule agonists. WO05012331 and WO05012232 disclose macrocyclic compounds which are agonists or antagonists of mammalian motilin or ghrelin receptors. WO06127252 discloses erythromycin derivatives.

WO07/007,018 describes compounds of formula (A), which have activity as agonists of the GPR38 receptor

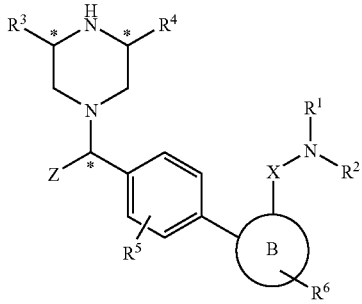

(A)

WO07/012,479 describes compounds of formula (B), which have activity as agonists of the GPR38 receptor

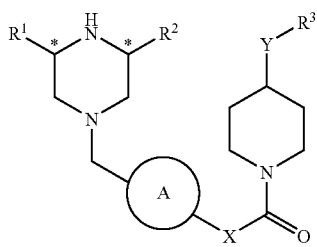

(B)

A structurally novel class of compounds has now been found which provides agonists of the GPR38 receptor.

The present invention therefore provides compounds of formula (I) or pharmaceutically acceptable or derivative thereof:

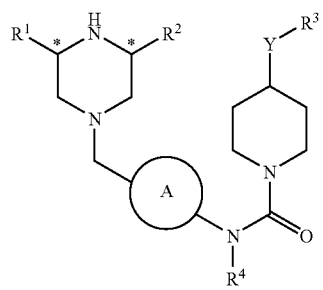

(I)

wherein
A is phenyl or a 6-membered heteroaryl ring, optionally substituted with halogen, $C_{(1-4)}$alkyl or $C_{(1-4)}$alkoxy;
$R^1$ and $R^2$ are independently H or $C_{(1-4)}$ alkyl;
$R^3$ is optionally substituted phenyl or optionally substituted 5 or 6 membered heteroaryl;
Y is NH, O, $CH_2$ or a bond;
$R^4$ is $C_{(1-4)}$ alkyl or $C_{(1-4)}$ alkoxy $C_{(1-4)}$ alkyl.

When $R^3$ is substituted, it may have 1, 2 or 3 substituents, each independently selected from halogen, $C_{(1-4)}$alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^5$, $NR^5R^6$, $NHCOR^5$, $NHSO_2R^5$, $C(O)CF_3$, $C(O)C_{(1-4)}$alkyl, $C(O)C_{(3-7)}$cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^5$, $CONR^5R^6$, $SOR^6$, $SO_2CF_3$, $SO_2R^6$, $OSO_2R^6$, $OSO_2CF_3$, $SO_2NH_2$, $SO_2NHR^5$, $SO_2NR^5R^6$, where $R^5$ and $R^6$ may be the same or different and represent $C_{(1-4)}$ alkyl, phenyl optionally substituted with halogen or 5 or 6 membered heteroaryl optionally substituted with halogen.

The term "alkyl" as a group or part of a group e.g. alkoxy or hydroxyalkyl refers to a straight or branched alkyl group in all isomeric forms. The term "$C_{(1-4)}$ alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, or tert-butyl, Examples of such alkoxy groups include methoxy, ethoxy, propoxy, iso-propoxy, butoxy, iso-butoxy, sec-butoxy and tert-butoxy.

Suitable $C_{3-7}$cycloalkyl groups include cyclopropyl, cyclobutyl, cyclopentyl and cyclohexyl.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents a 5 or 6 membered unsaturated aromatic ring which comprises one or more heteroatoms. When the term heteroaryl represents a 5 membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In one embodiment of the invention, A is phenyl or pyridyl.
In one embodiment of the invention, $R^1$ is hydrogen or methyl.
In one embodiment of the invention, $R^2$ is hydrogen or methyl.
In one embodiment of the invention, $R^3$ is optionally substituted phenyl.
In one embodiment of the invention, Y is NH, O or a bond.
In one embodiment of the invention, $R^4$ is methyl.
In one embodiment of the invention,
A is phenyl or pyridyl; and/or
$R^1$ is hydrogen or methyl; and/or
$R^2$ is hydrogen or methyl; and/or
$R^3$ is optionally substituted phenyl; and/or
Y is NH, O or a bond; and/or
$R^4$ is methyl.

When A is substituted it may be substituted by methyl.
When $R^3$ is substituted phenyl it may be substituted by one to two substituents selected from fluoro, cyano, aminocarbonyl and methoxy.

In a further embodiment of the invention the (piperazinyl)methylene substituent and (—$NR_4$—) are para- to each other across ring A.

In certain of the compounds of formula (I), dependent upon the nature of the substituent there are chiral carbon atoms, such as the carbon atom marked with an "*" and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses. Preferred compounds of formula (I) wherein $R^1$ and $R^2$ are both methyl are those wherein the piperazine C* carbons have the 3R,5S-configuration. Preferred compounds of formula (I) wherein one of $R^1$ and $R^2$ is methyl and the other is hydrogen are those wherein the piperazine C* carbon has the S-configuration.

Certain of the compounds herein can exist in various tautomeric forms and it is to be understood that the invention encompasses all such tautomeric forms.

Suitable compounds of the invention are:

4-[(3-fluorophenyl)amino]-N-methyl-N-(4-{[(3S)-3-methyl-1-piperazinyl]methyl}phenyl)-1-piperidinecarboxamide (E1)

4-[(4-fluorophenyl)amino]-N-methyl-N-(4-{[(3S)-3-methyl-1-piperazinyl]methyl}phenyl)-1-piperidinecarboxamide (E2)

4-[(3-cyanophenyl)amino]-N-methyl-N-(4-{[(3S)-3-methyl-1-piperazinyl]methyl}phenyl)-1-piperidinecarboxamide (E3)

4-[(2-fluorophenyl)amino]-N-methyl-N-(4-{[(3S)-3-methyl-1-piperazinyl]methyl}phenyl)-1-piperidinecarboxamide (E4)

4-[(4-cyanophenyl)amino]-N-methyl-N-(4-{[(3S)-3-methyl-1-piperazinyl]methyl}phenyl)-1-piperidinecarboxamide (E5)

4-{[2-(aminocarbonyl)phenyl]amino}-N-methyl-N-(4-{[(3S)-3-methyl-1-piperazinyl]methyl}phenyl)-1-piperidinecarboxamide (E6)

4-[(3-fluorophenyl)oxy]-N-methyl-N-(4-{[(3S)-3-methyl-1-piperazinyl]methyl}phenyl)-1-piperidinecarboxamide (E7)

4-[(2-cyanophenyl)amino]-N-methyl-N-(4-{[(3S)-3-methyl-1-piperazinyl]methyl}phenyl)-1-piperidinecarboxamide (E8)

4-{[3-fluoro-4-(methyloxy)phenyl]amino}-N-methyl-N-(4-{[(3S)-3-methyl-1-piperazinyl]methyl}phenyl)-1-piperidinecarboxamide (E9)

4-{[4-fluoro-3-(methyloxy)phenyl]amino}-N-methyl-N-(4-{[(3S)-3-methyl-1-piperazinyl]methyl}phenyl)-1-piperidinecarboxamide (E10)

4-[(3-fluorophenyl)amino]-N-methyl-N-(4-{[(3R)-3-methyl-1-piperazinyl]methyl}phenyl)-1-piperidinecarboxamide (E11)

N-(4-{[(3R,5S)-3,5-dimethyl-1-piperazinyl]methyl}phenyl)-4-[(3-fluorophenyl)amino]-N-methyl-1-piperidinecarboxamide (E12)

4-(3-cyanophenyl)amino]-N-methyl-N-[4-(1-piperazinylmethyl)phenyl]-1-piperidinecarboxamide (E13)

4-[(3-fluorophenyl)amino]-N-methyl-N-[4-(1-piperazinylmethyl)phenyl]-1-piperidinecarboxamide (E14)

4-[(4-fluorophenyl)amino]-N-methyl-N-[4-(1-piperazinylmethyl)phenyl]-1-piperidinecarboxamide (E15)

4-(4-fluorophenyl)-N-methyl-N-(4-{[(3S)-3-methyl-1-piperazinyl]methyl}phenyl)-1-piperidinecarboxamide (E16)

4-(3-fluorophenyl)-N-methyl-N-(4-{[(3S)-3-methyl-1-piperazinyl]methyl}phenyl)-1-piperidinecarboxamide (E17)

4-(3-cyanophenyl)-N-methyl-N-(4-{[(3S)-3-methyl-1-piperazinyl]methyl}phenyl)-1-piperidinecarboxamide (E18)

4-[(3-fluorophenyl)amino]-N-methyl-N-(3-methyl-4-{[(3S)-3-methyl-1-piperazinyl]methyl}phenyl)-1-piperidinecarboxamide (E19)

4-[(3-fluorophenyl)amino]-N-methyl-N-(6-{[(3S)-3-methyl-1-piperazinyl]methyl}-3-pyridinyl)-1-piperidinecarboxamide (E20)

4-{[4-(aminocarbonyl)phenyl]amino}-N-methyl-N-(4-{[(3S)-3-methyl-1-piperazinyl]methyl}phenyl)-1-piperidinecarboxamide (E21)

4-[(4-cyanophenyl)amino]-N-methyl-N-[4-(1-piperazinylmethyl)phenyl]-1-piperidinecarboxamide (E22)

One embodiment of a compound of formula (I) is 4-[(3-fluorophenyl)amino]-N-methyl-N-(4-{[(3S)-3-methyl-1-piperazinyl]methyl}phenyl)-1-piperidinecarboxamide or a salt thereof.

Included within the scope of the "compounds of the invention" are all salts, solvates, hydrates, complexes, polymorphs, prodrugs, radiolabelled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also includes isotopically-labelled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I. Compounds of the invention that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the invention can generally be prepared by carrying out the procedures disclosed in the Schemes and/or in the Examples below, then substituting a readily available isotopically labelled reagent for a non-isotopically labelled reagent.

In a further aspect, this invention provides a process for the preparation of a compound of formula (I):

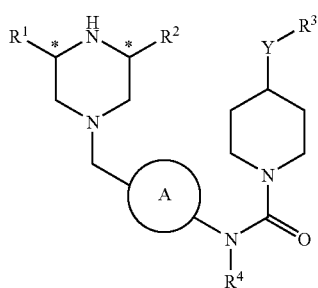

(I)

wherein $R^1$, $R^2$, $R^3$, $R^4$, A and Y are as herein before defined or a pharmaceutically acceptable salt or solvate thereof, which process comprises reacting of a compound of formula (II):

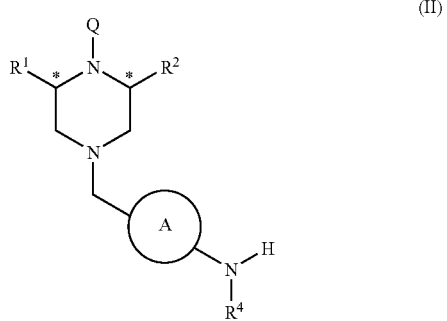

(II)

wherein $R^1$, $R^2$, $R^4$ and A are as defined in formula (I) and Q is hydrogen or a suitable nitrogen protecting group such as tert-butyloxycarbonyl (BOC) or benzyloxycarbonyl (CBZ), with a compound of formula (III):

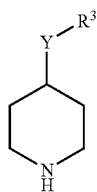

(III)

wherein Y and $R^3$ are as defined in formula (I), using reaction conditions suitable for urea formation; for example, in the presence phosgene or carbonyl diimidazole and a suitable base such as triethylamine and in a suitable solvent such as 1,2-dichloroethane or dichloromethane.

And thereafter optionally carrying out one or more of the following reactions:

1. Converting one compound of formula (I) into another compound of formula (I);
2. Removing any protecting group;
3. Forming a suitable pharmaceutically acceptable salt or solvate of the compound so formed.

Compounds of formula (III), where Y=NH, may be prepared by a reductive amination reaction which involves reacting a suitable aniline derivative, $R^3$—NH$_2$, with a suitably protected piperidin-4-one, such as 1-(tert-butoxycarbonyl) piperidin-4-one, in the presence of a reducing agent such as sodium tri(acetoxy)borohydride, in a suitable solvent such as 1,2-dichloroethane, followed by removal of the nitrogen protecting group by conventional techniques as described below.

Compounds of formula (III), where Y=NH, may also be prepared by an arylation reaction which involves reacting a suitable aryl halide, for example $R^3$—Br, with a suitably protected 4-aminopiperidine such as (1-tert-butoxycarbonyl)-4-aminopiperidine, in the presence of a suitable catalyst system such as palladium (II) acetate/BINAP, in a suitable solvent such as 1,4-dioxane, followed by removal of the nitrogen protecting group by conventional techniques as described below.

Compounds of formula (III), where Y=O, may be prepared by an alkylation reaction which involves reacting a suitable phenol derivative, $R^3$—OH, with a suitably protected 4-hydroxypiperidine, such as 1-(tert-butoxycarbonyl)-4-hydroxypiperidine, in the presence of triphenylphosphine and diisopropylazodicarboxylate, in a suitable solvent such as tetrahydrofuran, followed by removal of the nitrogen protecting group by conventional techniques as described below.

Compounds of formula (II) wherein A represents a 1,4-phenylene group may be prepared by reaction of a compound of formula (IV):

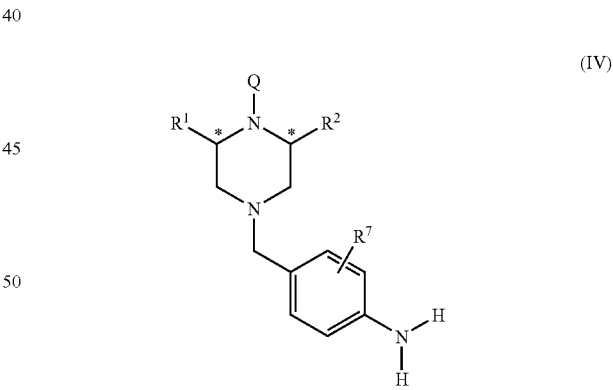

(IV)

wherein $R^1$ and $R^2$ are as defined in formula (I), $R^7$ represents optional substitution in the phenylene moiety as defined for A above, and Q is hydrogen or a suitable nitrogen protecting group such as tert-butyloxycarbonyl (BOC) or benzyloxycarbonyl (CBZ) with an appropriate aldehyde or ketone to provide $R^4$, using conditions suitable for a reductive amination; for example in the presence of a suitable reducing agent such as sodium borohydride, in a suitable solvent such as methanol and optionally in the presence of a suitable base such as sodium methoxide.

Compounds of formula (IV) may be prepared by reaction of a compound of formula (V):

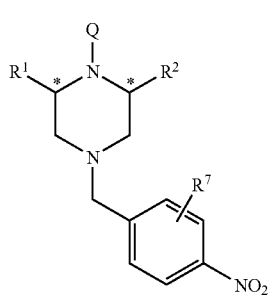

(V)

wherein $R^1$ and $R^2$ are as defined in formula (I), $R^7$ represents optional substitution in the phenylene moiety as defined for A above, and Q is hydrogen or a suitable nitrogen protecting group such as tert-butyloxycarbonyl (BOC) or benzyloxycarbonyl (CBZ), using conditions suitable for a reduction; for example when Q is BOC, hydrogenation in the presence of a suitable catalyst such as palladium on charcoal or platinum on charcoal, in a suitable solvent such as methanol and in the presence of a suitable base such as potassium hydroxide or triethylamine. Alternatively when Q is BOC or CBZ, the reduction may be carried out using a suitable metal reducing agent such as iron powder, in the presence of a suitable proton source such as ammonium chloride and in a suitable solvent such as aqueous methanol.

Compounds of formula (V) may be prepared by reaction of a compound of formula (VI):

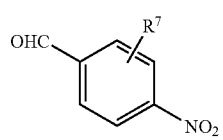

(VI)

wherein $R^7$ represents optional substitution in the phenylene moiety as defined for A above with a compound of formula (VII):

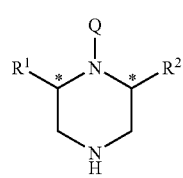

(VII)

wherein $R^1$ and $R^2$ are as defined in formula (I) and Q is hydrogen or a suitable nitrogen protecting group such as tert-butyloxycarbonyl (BOC) or benzyloxycarbonyl (CBZ), using reaction conditions suitable for a reductive amination, for example in the presence of a reducing agent such as sodium tri(acetoxy)borohydride in a suitable solvent such as dichloromethane or 1,2-dichloroethane.

Compounds of formula (VI) and (VII) are commercially available.

An alternative process for preparation of compounds of formula (II) wherein A represents a 2,5-pyridyl group comprises reaction of a compound of formula (VII) as defined above with a compound of formula (VIII):

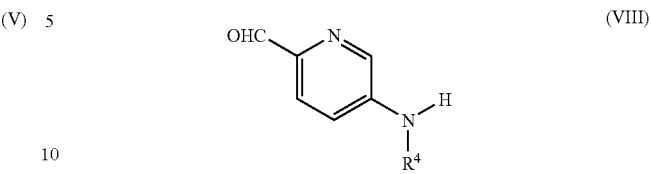

(VIII)

wherein $R^4$ is as defined in formula (I), under conditions suitable for reductive amination as described above.

Compounds of formula (VIII) may be prepared by reaction of a compound of formula (IX):

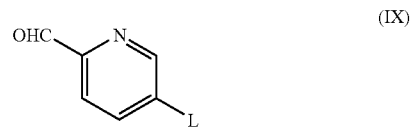

(IX)

wherein L represents a leaving group such as halogen (e.g. bromine) with a compound of formula $R^4NHQ^1$, wherein $R^4$ is as defined in formula (I) and $Q^1$ is a suitable nitrogen protecting group such as tert-butyloxycarbonyl (BOC), in the presence of a suitable transition metal catalyst system such as tris(dibenzylideneacetone) dipalladium(0)/xantphos, in the presence of a suitable base such as cesium carbonate and in a suitable solvent such as dioxane; followed by a suitable deprotection step.

Compounds of formula (IX) are commercially available

An alternative process for preparation of compounds of formula (IV) comprises reaction of a compound of formula (VII) as defined above with a compound of formula (X):

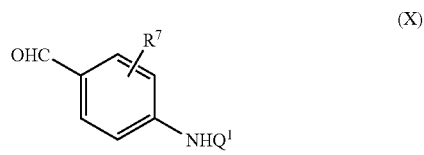

(X)

wherein $R^7$ represents optional substitution in the phenylene moiety as defined for A above and $Q^1$ is a suitable protecting group such as acetyl under conditions suitable for reductive amination as described above, followed by a suitable deprotection step to remove $Q^1$.

Compounds of formula (X) are commercially available or may be prepared from the corresponding carboxylic acid, using general methods for the conversion of a carboxylic acid to an aldehyde. See, for example, M. B. Smith & J. March, Advanced Organic Chemistry, 5th Edition, J Wiley & Sons, 2001, Chapter 19, p. 1506-1604.

It will be appreciated by those skilled in the art that it may be necessary to protect certain reactive substituents during some of the above procedures. Standard protection and deprotection techniques, such as those described in Greene T. W. & Wuts P. G. M., Protective groups in organic synthesis, $2^{nd}$ Edition, New York, Wiley (1991), can be used. For example, primary and secondary amines can be protected as phthalimide, trifluoroacetyl, benzyl, tert-butyloxycarbonyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as tert-butyloxycarbonyl may be removed using an acid such as hydrochloric or trifluoroacetic acid in a suitable solvent such as dichloromethane, diethyl ether, 1,4-dioxane, isopropanol or mixtures thereof.

Salts may be prepared conventionally by reaction with the appropriate acid or acid derivative.

The present invention also provides compounds of formula (II) as shown above wherein $R^1$, $R^2$, $R^4$ and A are as defined for formula (I), and Q is hydrogen or a suitable protecting group such as tert-butyloxycarbonyl (BOC) or benzyloxycarbonyl (CBZ). These compounds are useful as intermediates in the preparation of compounds of the present invention.

The potencies and efficacies of the compounds of this invention for GPR38 can be determined by FLIPR assay performed on the human cloned receptor as described herein. Compounds of formula (I) have demonstrated partial or full agonist activity at the GPR38 receptor, using the FLIPR (FLuorometric Imaging Plate Reader) functional assay described herein.

Compounds of formula (I) or pharmaceutically acceptable salts thereof are therefore of use in the treatment of conditions or disorders which are mediated via the GPR38 receptor. In particular the compounds of formula (I) or pharmaceutically acceptable salts thereof are of use in the treatment of certain gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, or in enterally fed patients, cachexia associated with advanced diseases such as cancer and/or the treatment thereof, and other disorders such as incontinence (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the GPR38 receptor. In particular the invention provides a compound of formula (I) or a pharmaceutically acceptable salt thereof for use as a therapeutic substance in the treatment of gastrointestinal disorders such as gastroesophageal reflux disorders, functional dyspepsia, irritable bowel syndrome, constipation, intestinal pseudo-obstruction, paralytic ileus following surgery or other manipulation, emesis, gastric stasis or hypomotility caused by various diseases such as diabetes and/or by the administration of other drugs, Crohn's disease, colitis, or in enterally fed patients, cachexia associated with advanced diseases such as cancer and/or the treatment thereof, and other disorders such as incontinence.

The invention further provides a method of treatment of conditions or disorders in mammals including humans which can be mediated via the GPR38 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the GPR38 receptor In order to use the compounds of formula (I) or pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) and pharmaceutically acceptable salts thereof may also be formulated in rectal compositions such as suppositories or retention enemas, e.g. containing conventional suppository bases such as cocoa butter or other glycerides.

The compounds of formula (I) and pharmaceutically acceptable salts thereof may also be formulated as depot preparations. Such long acting formulations may be administered by implantation (for example subcutaneously or intramuscularly) or by intramuscular injection. Thus, for example, the compounds of formula (I) or pharmaceutically acceptable salts thereof may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg or 1.0 to 200 mg, and such unit doses may be administered more than once a day, for example two or three times a day. Such therapy may extend for a number of weeks or months.

The compounds of formula (I) and pharmaceutically acceptable salts thereof may be used in combination preparations. For example, the compounds of the invention may be used in combination with one or more compounds with activity in reducing gastric acid; one or more compounds with activity in reducing gastro-esophageal reflux; one or more compounds with activity in reducing esophago-gastric irritancy or inflammation, especially when used to alleviate erosive or non-erosive esophagitis; one or more compounds with analgesic activity; and/or one or more compounds with mixed activity on motility and pain.

Examples of compounds with activity in reducing gastric acid include H2 receptor antagonists, acid pump antagonists and proton pump inhibitors. Examples of compounds with activity in reducing gastro-esophageal reflux include agonists at GABA-B. Examples of compounds with analgesic activity include compounds active at Neurokinin receptors (NK1, 2, 3), TRPV1 and sodium-channels. Examples of compounds with mixed activity on motility and pain include CRF2 antagonists, 5-HT3 antagonists or octreotide or other molecules active at sst2 receptors.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Conditions, Hardware and Software for Analytical LCMS Systems (I)
Hardware
Agilent 1100 Gradient Pump
Agilent 1100 Autosampler
Agilent 1100 DAD Detector
Agilent 1100 Degasser
Agilent 1100 Oven
Agilent 1100 Controller
Waters ZQ Mass Spectrometer
Sedere Sedex 55, Sedere Sedex 85 or Polymer Labs PL-ELS-2100
Software
Waters MassLynx version 4.0 SP2
Column
The column used is a Waters Atlantis, the dimensions of which are 4.6 mm×50 mm. The stationary phase particle size is 3 μm.
Solvents
A: Aqueous solvent=Water+0.05% Formic Acid
B: Organic solvent=Acetonitrile+0.05% Formic Acid
Method
The generic method used has a 5 minute runtime.
Time/min % B
0 3
0.1 3
4 97
4.8 97
4.9 3
5.0 3
Flow Rate
The above method has a flow rate of 3 ml/mins
(II)
Hardware
Waters Acquity Binary Solvent Manager
Waters Acquity Sample Manager
Waters Acquity PDA
Waters ZQ Mass Spectrometer
Sedere Sedex 85, Sedere Sedex 75, Polymer Labs PL-ELS-2100
Software
Waters MassLynx version 4.1
Column The column used is a Waters Acquity BEH HPLC C18, the dimensions of which are 2.1 mm×50 mm. The stationary phase particle size is 1.7 μm.
Solvents
A: Aqueous solvent=Water+0.05% Formic Acid
B: Organic solvent=Acetonitrile+0.05% Formic Acid
Weak Wash=1:1 Methanol:Water
Strong Wash=Water
Method
The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40 deg
The UV detection range is from 220 to 330 nm
Conditions for Open Access Mass Directed Auto Prep System (MDAP)
(I)
Hardware
Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System;
Software
MicroMass MassLynx v4.0
Column
The column used is typically a Supelco LCABZ++ column whose dimensions are 20 mm internal diameter by 100 mm in length. The stationary phase particle size is 5 μm.
Solvents
A: Aqueous solvent=Water+0.1% Formic Acid
B: Organic solvent=MeCN:Water 95:5+0.05% Formic Acid
Make up solvent=MeOH:Water 80:20+50 mMol Ammonium Acetate
Needle rinse solvent=MeOH:Water:DMSO 80:10:10
Methods
One of five methods may be used depending on the analytical retention time of the compound of interest.
All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate
All of the above methods have a flow rate of 20 ml/min.
(II)
Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector
Software
Waters MassLynx version 4 SP2
Column
The columns used are Waters Atlantis, the dimensions of which are 19 mm×100 mm (small scale) and 30 mm×100 mm (large scale). The stationary phase particle size is 5 μm.
Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods
There are five methods used depending on the analytical retention time of the compound of interest. They have a 13.5-minute runtime, which comprises of a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)
Flow Rate
All of the above MDAP methods have a flow rate of either 20 mls/min (Small Scale) or 40 mls/min (Large Scale).
Shallow Gradients
Large 1.5 to 2.3 min=13-29% B
Large 1.9 to 2.3 min=25-41% B
Large 2.3 to 2.6 min=37-53% B
Large 2.6 to 3.1 min=49-65% B
Large 3.1 to 3.6 min=61-77% B
Conditions Used for NMR
Hardware
Bruker 400 MHz Ultrashield
Bruker B-ACS60 Autosampler
Bruker Advance 400 Console
Bruker DPX250
Bruker AVANCE 500
Bruker DRX600
Software
User interface—NMR Kiosk
Controlling software—XWin NMR version 3.0
Chromatography
Unless stated otherwise, all column chromatography was carried out using silica columns
Abbreviations
BINAP—(±)-2,2'-bis(diphenylphosphino)-1,1'-binaphthalene
$^tBuOH$—tert-butanol
$CDCl_3$—deuteriochloroform
$CD_3OD$—methanol-$d_4$
1,2-DCE—1,2-dichloroethane,
DCM—dichloromethane
DMSO-$d_6$—dimethyl sulfoxide-$d_6$
$Et_2O$—diethyl ether
EtOAc—ethyl acetate
EtOH—ethanol
HCl—hydrochloric acid, hydrogen chloride
IMS—industrial methylated spirit
KOH—potassium hydroxide MeOH—methanol
MgSO$_4$—magnesium sulfate
MnO$_2$—manganese dioxide
NaCl—sodium chloride
NaHCO$_3$—sodium hydrogen carbonate
NaOH—sodium hydroxide
Na$_2$SO$_4$—sodium sulfate
NH$_3$—ammonia
Pd/C—palladium on charcoal
Pt/C—platinum on charcoal
SCX—strong cation exchanger
TFA—trifluoroacetic acid
THF—tetrahydrofuran
Xantphos—4,5-bis(diphenylphosphino)-9,9-dimethylxanthene

Description 1

1,1-Dimethylethyl 4-[(4-fluorophenyl)amino]-1-piperidinecarboxylate (D1)

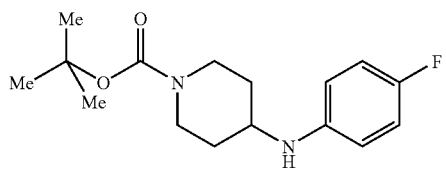

A mixture of 1,1-dimethylethyl 4-oxo-1-piperidinecarboxylate (1 g, 5 mmol), 4-fluoroaniline (0.56 g, 5 mmol) and acetic acid (0.26 ml, 5 mmol) in 1,2-DCE (30 ml) was stirred at room temperature for 24 h. Sodium tri(acetoxy)borohydride (1.48 g, 7 mmol) was then added and stirring continued for 24 h. The reaction mixture was washed with water, dried (MgSO$_4$) and then concentrated in vacuo to give the title compound as a crude solid (1.6 g). δ$_H$ (CDCl$_3$, 250 MHz) 6.88 (2H, t), 6.54 (2H, dd), 4.04 (2H, m), 3.35 (1H, m), 2.91 (2H, m), 2.02 (2H, m), 1.46 (9H, s), 1.30 (2H, m).

Description 2

N-(4-Fluorophenyl)-4-piperidinamine (D2)

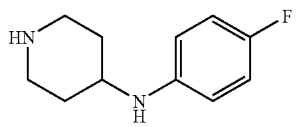

A solution of 1,1-dimethylethyl 4-[(4-fluorophenyl)amino]-1-piperidinecarboxylate (D1) (1.6 g) in 2M HCl (5 ml) and 1,4-dioxane (20 ml) was heated at 60° C. for 24 h. On cooling, the solution was diluted with water, basified with 2M NaOH solution and extracted with EtOAc (×3). The combined organics were dried (MgSO$_4$) and concentrated in vacuo to give the title compound as a yellow oil (0.71 g). δ$_H$ (CDCl$_3$, 250 MHz) 6.88 (2H, t), 6.54 (2H, dd), 3.30 (1H, m), 3.20 (2H, m), 2.70 (2H, m), 2.05 (2H, m), 1.69 (2H, br), 1.29 (2H, m).

Description 3

1,1-Dimethylethyl 4-[(3-fluorophenyl)amino]-1-piperidinecarboxylate (D3)

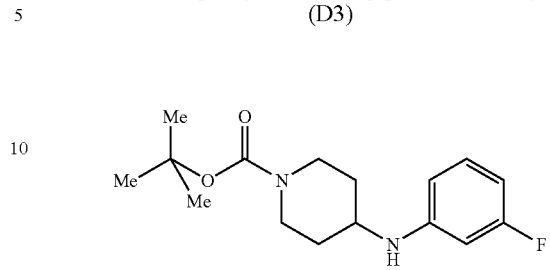

A mixture of 1,1-dimethylethyl 4-oxo-1-piperidinecarboxylate (1.91 g, 9.53 mmol), 3-fluoroaniline (1.06 g, 9.53 mmol) and acetic acid (0.55 ml, 9.53 mmol) in 1,2-DCE (50 ml) was stirred at room temperature overnight. Sodium tri(acetoxy)borohydride (2.82 g, 13.3 mmol) was then added and the reaction mixture was stirred for 8 h, then allowed to stand at room temperature. The reaction mixture was diluted with DCM and washed with NaHCO$_3$ solution, dried over MgSO$_4$ and then concentrated to give the product which was purified by column chromatography. Elution with 0-40% EtOAc/pentane gave the title compound as a white solid (2.3 g). δ$_H$ (CDCl$_3$, 250 MHz) 7.08 (1H, q), 6.35 (3H, m), 4.04 (1H, br s), 3.65 (1H, br s), 3.38 (1H, m), 2.92 (2H, m), 2.02 (2H, m), 1.47 (9H, s), 1.34 (2H, m).

Description 4

N-(3-Fluorophenyl)-4-piperidinamine (D4)

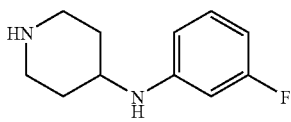

A solution of 1,1-dimethylethyl 4-[(3-fluorophenyl)amino]-1-piperidinecarboxylate (D3) (2.30 g) in 2M HCl (5 ml) and 1,4-dioxane (40 ml) was heated at 70° C. with stirring overnight. On cooling, the solvent was removed in vacuo and the residue diluted with 2M NaOH solution and extracted with 9:1 EtOAc/$^t$BuOH (×2). The organics were dried (MgSO$_4$) and concentrated in vacuo to give the title compound as a yellow solid (1.33 g). δ$_H$ (CDCl$_3$, 250 MHz) 7.07 (1H, q), 6.33 (3H, m), 3.83 (1H, br s), 3.33 (1H, br s), 3.12 (2H, m), 2.71 (2H, m), 2.04 (2H, m), 1.30 (2H, m).

Description 4a

N-(3-Fluorophenyl)-4-piperidinamine hydrochloride (D4a)

3-Fluoroaniline (28.38 ml, 0.296 mol) was added to a solution of 4-oxo-1-piperidine carboxylate (60 g, 0.302 mol) in 1,2-DCE (600 ml) and the mixture stirred for 15 minutes. Sodium tri(acetoxy)borohydride (83 g, 0.392 mol) was added gradually over 5 minutes and the mixture stirred for 5.5 h, then poured into a mixture of 2M HCl (100 ml), water (200 ml) and ice (1 l). The phases were separated and the aqueous phase extracted with DCM (200 ml). The combined organic phases were dried over MgSO$_4$ and concentrated to give a pale yellow solid which was dissolved in MeOH (400 ml) and treated with 2M HCl (100 ml). The resulting solution was stirred at 60° C. overnight. 5M HCl (100 ml) was added and heating continued for a further 7 h. The reaction mixture was concentrated in vacuo to give a yellow oily solid. This was re-crystallized from MeOH/EtOAc to give two batches of the title compound (42.6 g & 17.0 g). These batches were then re-crystallized from IMS/EtOAc and the resulting batches were dried in vacuo at 50° C. to give the title compound (49.0 g total). $\delta_H$ (CD$_3$OD, 250 MHz) 7.54 (1H, q), 7.24 (2H, m), 7.15 (1H, t), 3.89 (1H, m), 3.54 (2H, d), 3.11 (2H, t), 2.24 (2H, d), 2.01 (2H, m).

Description 5

1,1-Dimethylethyl 4-[(3-cyanophenyl)amino]-1-piperidinecarboxylate (D5)

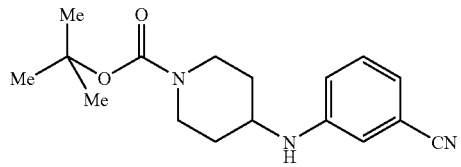

A mixture of BINAP (560 mg, 0.9 mmol), palladium acetate (135 mg, 0.6 mmol) and cesium carbonate (2.932 g, 9 mmol) in 1,4-dioxane (10 ml) was sonicated for 50 minutes. 1,1-Dimethylethyl 4-amino-1-piperidinecarboxylate (1.2 g, 6 mmol) and 3-bromobenzonitrile (1.638 g, 9 mmol) were added and the mixture heated to 105° C. overnight under an argon atmosphere. On cooling, the solvent was removed in vacuo and the residue partitioned between water (100 ml) and EtOAc (100 ml). The organic layer was separated, dried and concentrated and the crude product purified by column chromatography. Elution with a 0-50% Et$_2$O/petroleum ether gradient gave the title compound as a white solid (1.49 g). $\delta_H$ (CDCl$_3$, 250 MHz) 7.22 (1H, t), 6.95 (1H, dd), 6.77 (2H, m), 4.07 (2H, m), 3.77 (1H, m), 3.41 (1H, m), 2.93 (2H, m), 2.03 (2H, m), 1.47 (9H, s), 1.34 (2H, m). MS (ES): MH$^+$ 302.

Description 6

3-(4-Piperidinylamino)benzonitrile (D6)

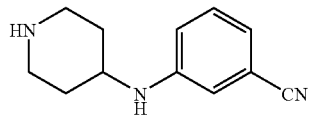

A solution of 1,1-dimethylethyl 4-[(3-cyanophenyl) amino]-1-piperidinecarboxylate (D5) (750 mg, 2.43 mmol) in DCM (30 ml) was cooled in an ice bath and TFA (6 ml) was added. The reaction mixture was then stirred at room temperature for 1 h. The solvent was removed in vacuo and the residue loaded onto an Isolute SCX cartridge. Elution with MeOH (100 ml) followed by 2M NH$_3$ in MeOH (100 ml) gave the title compound as a white solid (613 mg). $\delta_H$ (CDCl$_3$, 250 MHz) 7.21 (2H, t), 6.93 (1H, m), 6.77 (2H, m), 3.78 (1H, m), 3.35 (1H, m), 3.14 (2H, m), 2.73 (2H, m), 2.06 (2H, m), 1.34 (2H, m). MS (ES): MH$^+$ 202.

Description 7

1,1-Dimethylethyl 4-[(4-cyanophenyl)amino]-1-piperidinecarboxylate (D7)

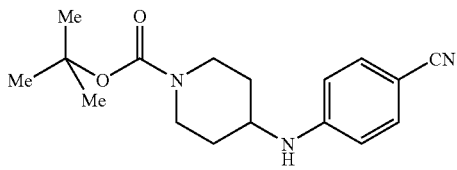

The title compound was prepared from 1,1-dimethylethyl 4-amino-1-piperidinecarboxylate and 4-bromobenzonitrile using a method similar to that described for D5 in Description 5.

Description 8

4-(4-Piperidinylamino)benzonitrile (D8)

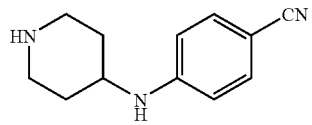

The title compound was prepared from 1,1-dimethylethyl 4-[(4-cyanophenyl)amino]-1-piperidinecarboxylate (D7) using a method similar to that described for D6 in Description 6 although purification by column chromatography was also carried out.

Description 9

1,1-Dimethylethyl 4-{[4-fluoro-3-(methyloxy)phenyl]amino}-1-piperidinecarboxylate (D9)

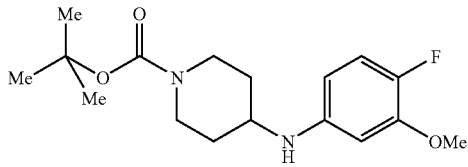

A solution of 1,1-dimethylethyl 4-oxo-1-piperidinecarboxylate (1.41 g, 7.1 mmol) and 4-fluoro-3-methoxyaniline (1 g, 7.1 mmol) was stirred at room temperature for 1 h. Sodium tri(acetoxy)borohydride (1.95 g, 9.2 mmol) was then added and stirring continued over-weekend. The reaction mixture was diluted with DCM, washed with saturated aqueous NaHCO$_3$ solution, dried and then concentrated in vacuo. Column chromatography eluting with 0-50% Et$_2$O/petroleum ether gave the title compound as a white solid (1.45 g). $\delta_H$ (CDCl$_3$, 400 MHz) 6.89 (1H, dd), 6.22 (1H, dd), 6.09 (1H, m), 4.03 (2H, br s), 3.84 (3H, s), 3.36 (1H, br s), 2.92 (2H, m), 2.03 (2H, m), 1.46 (9H, s), 1.32 (2H, m).

Description 10

N-[4-Fluoro-3-(methyloxy)phenyl]-4-piperidinamine (D10)

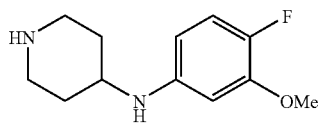

A solution of 1,1-dimethylethyl 4-{[4-fluoro-3-(methyloxy)phenyl]amino}-1-piperidinecarboxylate (D9) (1.45 g, 4.48 mmol) in DCM (16 ml) was cooled in an ice bath and TFA (4 ml) was added. The reaction mixture was stirred for 1 h, then warmed to room temperature and stirred for 2 h. The solvent was removed in vacuo and the residue partitioned between EtOAc and saturated aqueous NaHCO$_3$ solution. The organic phase was washed with further saturated aqueous NaHCO$_3$ solution. The aqueous was concentrated to ~50% volume, further basified with 2M NaOH solution and extracted with EtOAc (×2). All organic phases were combined and washed with further 2M NaOH solution, dried and concentrated to give the title compound as an orange gum (1 g). $\delta_H$ (DMSO-d$_6$, 400 MHz) 6.86 (1H, dd), 6.33 (1H, dd), 6.03 (1H, m), 5.32 (1H, d), 3.74 (3H, s), 3.33 (1H, br s), 3.18 (1H, m), 2.92 (2H, m), 2.51 (2H, m), 1.83 (2H, m), 1.17 (2H, m). MS (ES): MH$^+$ 225.

Description 11

1,1-Dimethylethyl 4-[(3-fluorophenyl)oxy]-1-piperidinecarboxylate (D11)

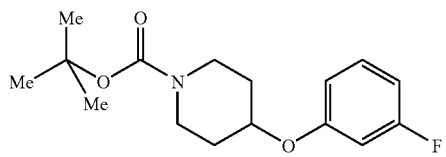

To a solution of 1,1-dimethylethyl 4-hydroxy-1-piperidinecarboxylate (24 g, 112 mmol), 3-fluorophenol (5.6 g, 59 mmol) and triphenylphosphine (31.4 g, 118 mmol) in THF (100 ml) was added di-isopropylazodicarboxylate (23.3 ml, 118 mmol). The reaction was stirred at room temperature over-weekend and then the solvent was removed in vacuo. The residue was diluted with DCM, hexane was added and the resultant precipitate was filtered off. The filtrate was concentrated in vacuo and purified by column chromatography. Elution with DCM gave the title compound (16.4 g, 87% pure). $\delta_H$ (CDCl$_3$, 250 MHz) 1.47 (9H, s), 1.76 (2H, m), 1.92 (2H, m), 3.35 (2H, ddd), 3.69 (2H, ddd), 4.44 (1H, m), 6.65 (3H, m), 7.20 (1H, m).

Description 12

4-[(3-Fluorophenyl)oxy]piperidine (D12)

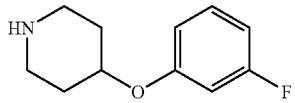

A solution of 1,1-dimethylethyl 4-[(3-fluorophenyl)oxy]-1-piperidinecarboxylate (D11) (16.4 g, 55 mmol) in DCM (200 ml) at 0° C. was treated with TFA (17 ml). The reaction was warmed to room temperature and stirred overnight. The solvent was then removed in vacuo and the residue partitioned between DCM and 2M NaOH solution. The aqueous was further extracted with DCM (×2) and the combined organics concentrated in vacuo. The residue was re-dissolved in DCM and extracted with 2M HCl (×2) which was then basified with 2M NaOH and re-extracted with DCM (×3). The combined organics were concentrated in vacuo to give the title compound (12 g). $\delta_H$ (CDCl$_3$, 250 MHz) 1.66 (2H, m), 2.01 (2H, m), 2.73 (2H, m), 3.14 (2H, m), 4.34 (1H, m), 6.68 (3H, m), 7.19 (1H, m), MS (ES): MH$^+$ 196. This whole was diluted with MeOH and treated with 1M HCl in Et$_2$O to give the hydrochloride salt of the title compound (8.0 g).

Description 13

1,1-Dimethylethyl 4-{[3-fluoro-4-(methyloxy)phenyl]amino}-1-piperidinecarboxylate (D13)

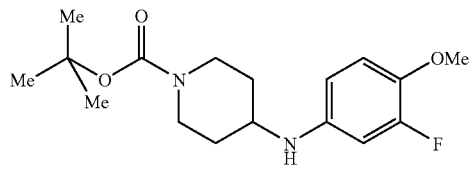

The title compound was prepared from 1,1-dimethylethyl 4-oxo-1-piperidinecarboxylate and 3-fluoro-4-methoxyaniline using a method similar to that described for D9 in Description 9.

Description 14

N-[3-Fluoro-4-(methyloxy)phenyl]-4-piperidinamine (D14)

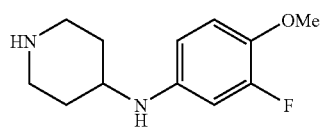

The title compound was prepared from 1,1-dimethylethyl 4-{[3-fluoro-4-(methyloxy)phenyl]amino}-1-piperidinecarboxylate (D13) using a method similar to that described for D10 in Description 10.

Description 15

1,1-Dimethylethyl 4-[(2-fluorophenyl)amino]-1-piperidinecarboxylate (D15)

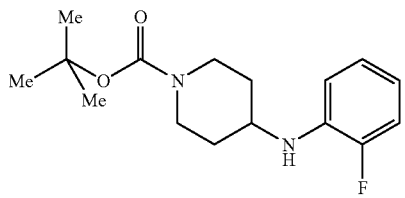

The title compound was prepared from 1,1-dimethylethyl 4-oxo-1-piperidinecarboxylate and 2-fluoroaniline using a method similar to that described for D3 in Description 3.

Description 16

N-(2-Fluorophenyl)-4-piperidinamine (D16)

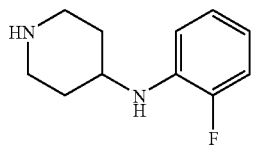

The title compound was prepared from 1,1-dimethylethyl 4-[(2-fluorophenyl)amino]-1-piperidinecarboxylate (D15) using a method similar to that described for D4 in Description 4.

Description 17

1,1-Dimethylethyl 4-[(2-cyanophenyl)amino]-1-piperidinecarboxylate (D17)

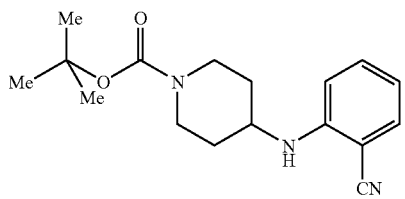

The title compound was prepared from 1,1-dimethylethyl 4-amino-1-piperidinecarboxylate and 2-bromobenzonitrile using a method similar to that described for D5 in Description 5.

Description 18

2-(4-Piperidinylamino)benzonitrile (D18)

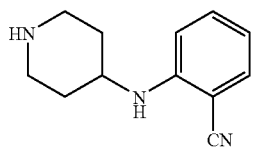

The title compound was prepared from 1,1-dimethylethyl 4-[(2-cyanophenyl)amino]-1-piperidinecarboxylate (D17) using a method similar to that described for D6 in Description 6.

Description 19

1,1-Dimethylethyl 4-{[2-(aminocarbonyl)phenyl]amino}-1-piperidinecarboxylate (D19)

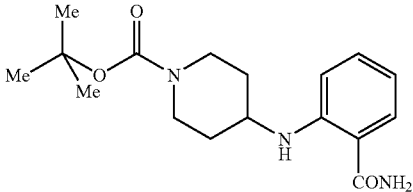

To a solution of 1,1-dimethylethyl 4-[(2-cyanophenyl)amino]-1-piperidinecarboxylate (D17) (355 mg, 1.18 mmol) in EtOH (6 ml) at 40° C. was added 2M NaOH solution (2.6 ml) followed by a mixture of hydrogen peroxide solution (27% w/w, 3.7 ml) in water (2.9 ml) and the reaction stirred for 2 h. Further hydrogen peroxide solution (27% w/w, 3.7 ml) in water (2.9 ml) was added and the reaction stirred at 40° C. for 1.5 h. Another portion of hydrogen peroxide solution (27% w/w, 7.4 ml) in water (5.8 ml) was added and stirring and heating were continued overnight. The reaction mixture was diluted with saturated aqueous NaCl solution (4 ml) and extracted with ᵗBuOH (5 ml). The organic extract was diluted with EtOAc (15 ml), dried (MgSO$_4$) and concentrated. Column chromatography eluting with 0-100% EtOAc/petroleum ether gave the title compound (150 mg). $\delta_H$ (CDCl$_3$, 250 MHz) 7.96 (1H, br d), 7.40 (1H, m), 7.31 (1H, m), 6.71 (1H, d), 6.57 (1H, t), 5.80 (2H, br s), 3.93 (2H, m), 3.53 (1H, m), 3.06 (2H, m), 1.99 (2H, m), 1.50 (2H, m), 1.47 (9H, s). MS (ES): MH$^+$ 320.

Description 20

2-(4-Piperidinylamino)benzamide (D20)

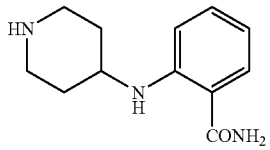

The title compound was prepared from 1,1-dimethylethyl 4-{[2-(aminocarbonyl)phenyl]amino}-1-piperidinecarboxylate (D19) using a method similar to that described for D6 in Description 6.

Description 21

1,1-Dimethylethyl (2S)-2-methyl-4-[(4-nitrophenyl)methyl]-1-piperazinecarboxylate (D21)

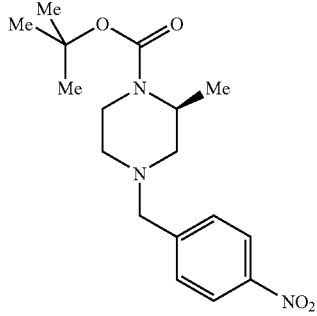

A mixture of 4-nitrobenzaldehyde (15.1 g, 0.1 mol), 1,1-dimethylethyl (2S)-2-methyl-1-piperazinecarboxylate hydrochloride (21.3 g, 0.09 mol), triethylamine (15 ml, 0.108 mol) and sodium tri(acetoxy)borohydride (42.4 g, 0.2 mol) in 1,2-DCE (500 ml) was stirred at room temperature overnight.

Saturated aqueous NaHCO₃ solution (200 ml) was added and the mixture stirred for 20-30 minutes. The phases were separated and the aqueous phase was washed with DCM. The combined organics were washed with brine, dried and concentrated. Column chromatography eluting with 0-20% EtOAc/hexane gave the title compound as a yellow oil which crystallized on standing (25.61 g). $\delta_H$ (CDCl₃, 400 MHz) 8.19 (2H, d), 7.53 (2H, d), 4.21 (1H, br.s), 3.83 (1H, d), 3.62 (1H, d), 3.50 (1H, d), 3.13 (1H, td), 2.74 (1H, m), 2.54 (1H, m), 2.20 (1H, dd), 2.08 (1H, m), 1.46 (9H, s), 1.25 (3H, d).

Description 21

Alternative Method (A)

1,1-Dimethylethyl (2S)-2-methyl-4-[(4-nitrophenyl)methyl]-1-piperazinecarboxylate (D21)

A mixture of 4-nitrobenzaldehyde (30.22 g, 0.2 mol), 1-dimethylethyl (2S)-2-methyl-1-piperazinecarboxylate (40.06 g, 0.2 mol) and sodium tri(acetoxy)borohydride (85 g, 0.4 mol) in 1,2-DCE (1 L) was stirred at room temperature over-weekend. The reaction mixture was treated portion-wise with NaHCO₃ solution (400 mL) over a period of ~2 h. After a further 30 minutes, the organic layer was separated, washed with brine, dried and concentrated to give a viscous pale yellow oil. Purification by column chromatography eluting with 0%, 10% and then 20% EtOAc/hexane yielded the title compound as a yellow crystalline solid (61.1 g).

Description 22

1,1-Dimethylethyl (2S)-4-[(4-aminophenyl)methyl]-2-methyl-1-piperazinecarboxylate (D22)

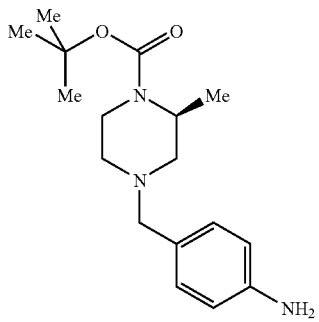

To 1,1-dimethylethyl (2S)-2-methyl-4-[(4-nitrophenyl)methyl]-1-piperazinecarboxylate (D21) (4.62 g, 13.78 mmol) and KOH (7.79 g, 138.8 mmol) in MeOH (100 mL) was added wet (50% w/w water) 10% Pd/C catalyst (4 g) and the mixture was hydrogenated at room temperature and atmospheric pressure for 40 minutes. The catalyst was removed by filtration and the filtrate concentrated in vacuo. The residue was partitioned between DCM and water and aqueous layer was further extracted with DCM (×2). The combined organics were washed with brine, dried and concentrated to give the title compound as a colourless gum (4.14 g) which was used in the next step without further purification. $\delta_H$ (CDCl₃, 400 MHz) 7.10 (2H, d), 6.64 (2H, d), 4.16 (1H, br.s), 3.78 (1H, d), 3.62 (2H, s), 3.42 (1H, d), 3.28 (1H, d), 3.08 (1H, td), 2.74 (1H, m), 2.58 (1H, m), 2.06 (1H, dd), 1.95 (1H, m), 1.46 (9H, s), 1.21 (3H, d).

Description 22

Alternative Method (A)

1,1-Dimethylethyl (2S)-4-[(4-aminophenyl)methyl]-2-methyl-1-piperazinecarboxylate (D22)

To a solution of potassium hydroxide (16.5 g, 0.29 mol) in water (35 mL) was added dry 10% Pd/C catalyst (10 g). MeOH (150 mL) was added and the mixture was hydrogenated at room temperature and atmospheric pressure for 15-20 minutes. 1,1-Dimethylethyl (2S)-2-methyl-4-[(4-nitrophenyl)methyl]-1-piperazinecarboxylate (D21) (10 g, 29.8 mmol) in MeOH (165 mL) was added and the reaction was hydrogenated for a total of 5 hrs. The catalyst was removed by filtration, washed with MeOH and water, and the filtrate/washings were concentrated in vacuo. The residue was partitioned between DCM and water and aqueous layer was further extracted with DCM. The combined organics were washed with brine, dried and concentrated to give the title compound as a colourless gum (8.49 g) which was used in the next step without further purification.

Description 22

Alternative Method (B)

1,1-Dimethylethyl (2S)-4-[(4-aminophenyl)methyl]-2-methyl-1-piperazinecarboxylate (D22)

A mixture of 1,1-dimethylethyl (2S)-2-methyl-4-[(4-nitrophenyl)methyl]-1-piperazinecarboxylate (D21) (21.62 g, 0.0644 mol), triethylamine (40 mL) and 5% Pt/C catalyst (21 g, 56% w/w water) in MeOH (400 mL) was hydrogenated at room temperature and atmospheric pressure overnight. The catalyst was removed by filtration and washed with further MeOH. The filtrate was concentrated in vacuo, re-dissolved in DCM (200 mL) and washed with 2M NaOH solution. The aqueous wash was re-extracted with DCM (×2, 100 mL) and all organic phases were combined, washed with brine, dried and concentrated to give the title compound (19.53 g) which was used in the next step without further purification.

Description 22

Alternative Method (C)

1,1-Dimethylethyl (2S)-4-[(4-aminophenyl)methyl]-2-methyl-1-piperazinecarboxylate (D22)

To 1,1-dimethylethyl (2S)-2-methyl-4-[(4-nitrophenyl)methyl]-1-piperazinecarboxylate (D21) (15 g, 44.8 mol) in MeOH (150 mL) and water (150 mL) at 80° C. was added ammonium chloride (11.9 g, 0.224 mol) and iron powder (7.5 g, 0.134 mol) with vigorous stirring. The reaction was stirred at 80° C. for 2 h then filtered through Celite® while still hot and the filter cake was washed with further DCM. The filtrate layers were separated and the aqueous layer was washed with DCM (×3). The DCM layers were combined, dried (Na₂SO₄) and concentrated to give the crude product which was purified by column chromatography. Elution with 20-70% EtOAc/petroleum ether gave the title compound as a white solid (9.46 g).

Description 23

1,1-Dimethylethyl (2S)-2-methyl-4-{[4-(methylamino)phenyl]methyl}-1-piperazinecarboxylate (D23)

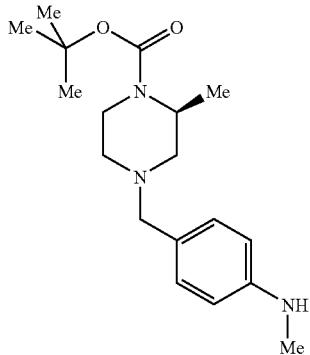

To 1,1-dimethylethyl (2S)-4-[(4-aminophenyl)methyl]-2-methyl-1-piperazinecarboxylate (D22) (4.14 g, 13.56 mmol) in dry MeOH (80 mL) at 50° C. under an argon atmosphere was added paraformaldehyde (1.22 g, 40.67 mmol) and sodium methoxide (3.65 g, 67.78 mmol). The mixture was stirred for ~24 h then sodium borohydride (1.54 g, 40.67 mmol) was added portion-wise and the reaction stirred at 50° C. overnight. After cooling to room temperature, acetone (10 mL) was added and the solvent removed in vacuo. The residue was partitioned between DCM and water and the organic phase was washed with brine, then dried and concentrated. Column chromatography gave the title compound as a colourless, crystalline solid (3.73 g). $\delta_H$ (CDCl$_3$, 400 MHz) 7.13 (2H, d), 6.57 (2H, d), 4.16 (1H, br.s), 3.78 (1H, d), 3.67 (1H, br.s), 3.42 (1H, d), 3.30 (1H, d), 3.08 (1H, td), 2.83 (3H, s), 2.75 (1H, m), 2.59 (1H, m), 2.06 (1H, dd), 1.94 (1H, m), 1.45 (9H, s), 1.21 (3H, d).

Description 23

Alternative Method (A)

1,1-Dimethylethyl (2S)-2-methyl-4-{[4-(methylamino)phenyl]methyl}-1-piperazinecarboxylate (D23)

A mixture of 1,1-dimethylethyl (2S)-4-[(4-aminophenyl)methyl]-2-methyl-1-piperazinecarboxylate (D22) (7.45 g, 24.43 mmol), paraformaldehyde (2.202 g, 73.28 mmol) and sodium methoxide (6.597 g, 122.13 mmol) in MeOH (150 mL) under an argon atmosphere was heated at 50° C. overweekend. After cooling, sodium borohydride (1.848 g, 48.85 mmol) was added and the reaction mixture was heated at 50° C. for 1 h then cooled to room temperature. Acetone was added until no more bubbling was observed, then the mixture was concentrated. The residue was partitioned between DCM and water and the aqueous was re-extracted with DCM. The combined organics were diluted with MeOH (approx 20 mL) to aid solubility, dried and concentrated to yield the title compound as an off white solid (7.77 g)

Description 24

1,1-Dimethylethyl (2R)-2-methyl-4-[(4-nitrophenyl)methyl]-1-piperazinecarboxylate (D24)

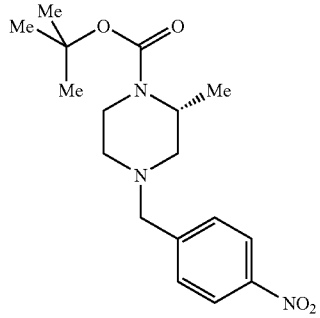

The title compound was prepared from 4-nitrobenzaldehyde and 1,1-dimethylethyl (2R)-2-methyl-1-piperazinecarboxylate using a method similar to that described for D21 in Description 21. MS (ES): [M-(CH$_2$=CMe$_2$)]H$^+$ 280.2, [M—(CH$_2$=CMe$_2$)—CO$_2$]H$^+$ 236.3, no molecular ion.

Description 25

1,1-Dimethylethyl (2R)-4-[(4-aminophenyl)methyl]-2-methyl-1-piperazinecarboxylate (D25)

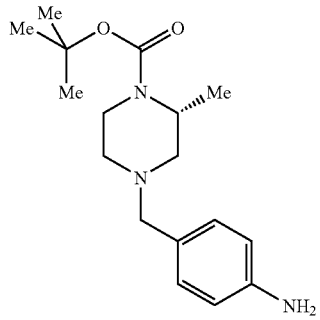

The title compound was prepared from 1,1-dimethylethyl (2R)-2-methyl-4-[(4-nitrophenyl)methyl]-1-piperazinecarboxylate (D24) using a method similar to that described for D22 in Description 22 although aqueous 2M KOH solution was used in place of solid KOH and the reaction time was 0.5 h. MS (ES): MH$^+$ 306.2, MNa$^+$ 328.2.

Description 26

1,1-Dimethylethyl (2R)-2-methyl-4-{[4-(methylamino)phenyl]methyl}-1-piperazinecarboxylate (D26)

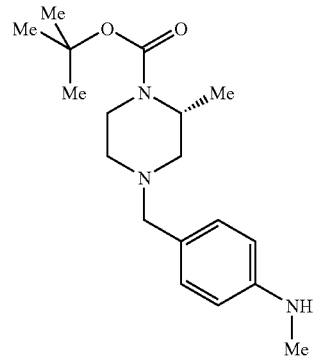

The title compound was prepared from 1,1-dimethylethyl (2R)-4-[(4-aminophenyl)methyl]-2-methyl-1-piperazinecarboxylate (D25) using a method similar to that described for D23 in Description 23A although the reaction was heated at 50° C. for 48 h prior to addition of sodium borohydride and for 1.5 h after addition. δ$_H$ (CDCl$_3$, 400 MHz) 7.13 (2H, d), 6.57 (2H, d), 4.16 (1H, m), 3.78 (1H, d), 3.42 (1H, d), 3.29 (1H, d), 3.08 (1H, td), 2.83 (3H, s), 2.75 (1H, m), 2.59 (1H, m), 2.07 (1H, dd), 1.94 (1H, m), 1.45 (9H, s), 1.21 (3H, d). MS (ES): 342.3 (MNa$^+$), no molecular ion (MH$^+$) observed.

Description 27

1,1-Dimethylethyl (2R,6S)-2,6-dimethyl-4-[(4-nitrophenyl)methyl]-1-piperazinecarboxylate (D27)

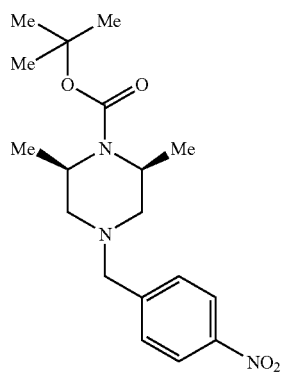

The title compound may be prepared using a method similar to that described for D21.

Description 27

Alternative Method (A)

1,1-Dimethylethyl (2R,6S)-2,6-dimethyl-4-[(4-nitrophenyl)methyl]-1-piperazinecarboxylate (D27)

(3R,5S)-1-[(4-Nitrophenyl)methyl]-3,5-dimethylpiperazine (D57) (4.278 g, 17.17 mmol) was dissolved in dioxane (180 mL) and Boc anhydride (7.494 g, 34.34 mmol) and saturated aqueous NaHCO$_3$ solution (60 mL) were added. The mixture was stirred at room temperature overnight; the mixture was filtered and the filter cake washed with DCM. The filtrate was concentrated under vacuum and the residue partitioned between DCM and water. The DCM layer was separated and the aqueous was extracted with DCM (×2). The DCM layers were combined and dried to produce a yellow oil (9.614 g). The mixture was purified by passing through an SCX cartridge to produce a yellow oil (4.787 g) which was a mixture of the title compound and unreacted D82. This whole was dissolved in DCM (60 mL) and triethylamine (2.936 mL) added followed by Boc anhydride (4.612 g, 21.13 mmol). The mixture was stirred at room temperature overnight under argon. PS-trisamine resin (6 g) was added and the mixture allowed to stir for 30 min; the polymer was filtered off and the solvent removed to produce a yellow oil (6.5621 g). Purification by column chromatography eluting with 0-50% Et$_2$O/petroleum ether gave a pale yellow solid (5.245 g). This solid was dissolved in MeOH and passed down an SCX cartridge (70 g) which was flushed with MeOH followed by 2M NH$_3$ in MeOH. The solvent was removed to produce a yellow solid (3.833 g) which was further purified by column chromatography. Elution with 0-50% Et$_2$O/petroleum ether gave the title compound as a whitish cream solid (2.624 g). MS (ES): 294.3, $^+$250.3, no molecular ion (MH$^+$) observed.

Description 28

1,1-Dimethylethyl (2R,6S)-4-[(4-aminophenyl)methyl]-2,6-dimethyl-1-piperazinecarboxylate (D28)

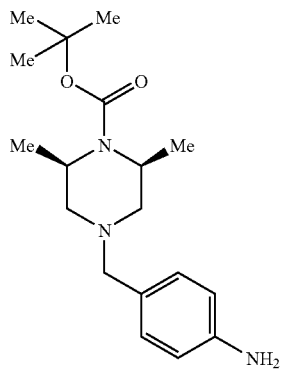

To a solution of 1,1-dimethylethyl (2R,6S)-2,6-dimethyl-4-[(4-nitrophenyl)methyl]-1-piperazinecarboxylate (D27) (2.62 g, 7.53 mmol) in MeOH (25 ml) and water (25 ml) heated to 80° C. was added iron powder (1.26 g, 22.54 mmol) and ammonium chloride (2.01 g, 37.58 mmol). The reaction was stirred vigorously at 80° C. for 1.5 h and then the iron residues removed by filtration through Celite®. The filtrate was concentrated and the residue partitioned between DCM and water. The aqueous layer was further extracted with DCM (×2) and the combined organics were dried and concentrated to give the crude product as a yellow foam (2.01 g). Column chromatography eluting with 0-100% Et$_2$O/petroleum ether gave the title compound (1.694 g). δ$_H$(CDCl$_3$, 400 MHz) 7.12 (2H, d), 6.64 (2H, d), 4.05 (2H, m), 3.64 (2H, br. s), 3.36 (2H, s), 2.59 (2 h, d), 2.06 (2H, dd), 1.46 (9H, s), 1.27 (6H, d). MS (ES): MH$^+$ 320.3, MNa$^+$ 342.3.

Description 29

1,1-Dimethylethyl (2R,6S)-2,6-dimethyl-4-{[4-(methylamino)phenyl]methyl}-1-piperazinecarboxylate (D29)

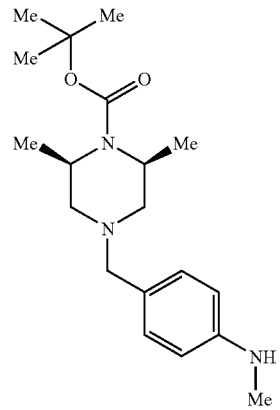

The title compound was prepared from 1,1-dimethylethyl (2R,6S)-4-[(4-aminophenyl)methyl]-2,6-dimethyl-1-piperazinecarboxylate (D28) using a method similar to that described for D23 in Description 23A although the reaction was heated at 50° C. for 48 h prior to addition of sodium borohydride then for 1 h after addition. Further paraformaldehyde (1 eq) and sodium methoxide (1 eq) were added; the reaction was heated at 50° C. for 12 h; further sodium borohydride (1 eq) was added and the reaction heated at 50° C. for 1 h. $\delta_H$ (CDCl$_3$, 400 MHz) 7.16 (2H, d), 6.57 (2H, d), 4.05 (2H, m), 3.70 (1H, br s), 3.36 (2H, s), 2.82 (3H, s), 2.59 (2H, d), 2.06 (2H, dd), 1.49 (9H, s), 1.27 (6H, d). MS (ES): 356.3, (MNa$^+$), 234.3, no molecular ion (MH$^+$) observed.

Description 30

1,1-Dimethylethyl 4-[(4-nitrophenyl)methyl]-1-piperazinecarboxylate (D30)

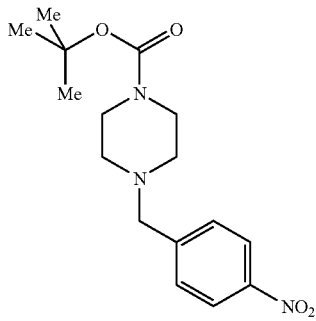

The title compound was prepared from 4-nitrobenzaldehyde and 1,1-dimethylethyl 1-piperazinecarboxylate using a method similar to that described for D21 in Description 21A although the product was purified by column chromatography followed by passing through an SCX column eluting with MeOH then 2M NH$_3$ in MeOH. MS (ES): 266.1, 222.2, no molecular ion (MH$^+$) observed.

Description 31

1,1-Dimethylethyl 4-[(4-aminophenyl)methyl]-1-piperazinecarboxylate (D31)

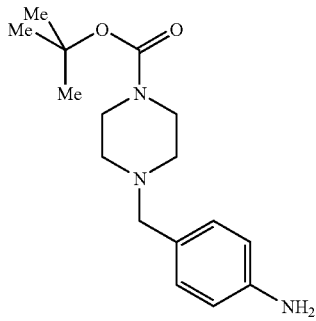

The title compound was prepared from 1,1-dimethylethyl 4-[(4-nitrophenyl)methyl]-1-piperazinecarboxylate (D30) using a method similar to that described for D28 in Description 28 although no column chromatography was required. MS (ES): MH$^+$ 292.1, MNa$^+$ 314.2.

Description 32

1,1-Dimethylethyl 4-{[4-(methylamino)phenyl]methyl}-1-piperazinecarboxylate (D32)

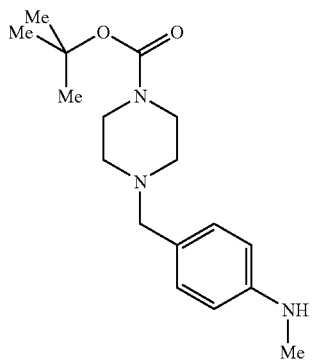

The title compound was prepared from 1,1-dimethylethyl 4-[(4-aminophenyl)methyl]-1-piperazinecarboxylate (D31) using a method similar to that described for D23 in Description 23A although the reaction was heated at 50° C. overnight prior to addition of sodium borohydride and no column chromatography was required. $\delta_H$ (CDCl$_3$, 400 MHz) 7.11 (2H, d), 6.57 (2H, d), 3.69 (1H, br.s), 3.40 (6H, m), 2.83 (3H, s), 2.36 (4H, m), 1.45 (9H, s) [$\delta$ values corrected for incorrectly referenced TMS at 0.58 ppm on spectrum]. MS (ES): 206.2, no molecular ion (MH$^+$) observed.

Description 33

1,1-Dimethylethyl (2S)-4-({4-[({4-[(3-fluorophenyl)amino]-1-piperidinyl}carbonyl)(methyl)amino]phenyl}methyl)-2-methyl-1-piperazinecarboxylate (D33)

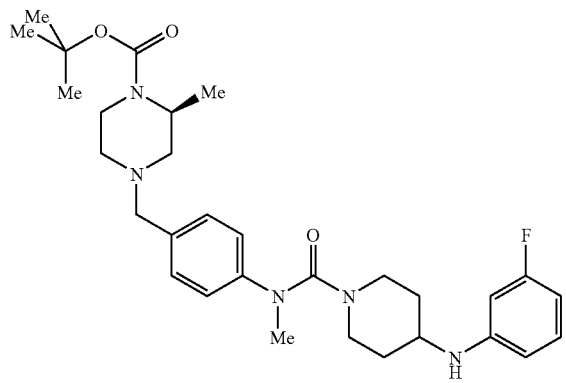

To a solution of 1,1-dimethylethyl (2S)-2-methyl-4-{[4-(methylamino)phenyl]methyl}-1-piperazinecarboxylate (D23) (0.12 g, 0.38 mmol) in DCM (5 ml) was added saturated aqueous NaHCO$_3$ solution (5 ml) and the mixture stirred vigorously for 10 minutes at 0° C. The mixture was allowed to stand and partition, then a solution of phosgene in toluene (0.398 ml, 20% in toluene, 0.752 mmol) was injected into the organic phase of the reaction mixture. The mixture was stirred for a further 10 minutes. The excess phosgene was removed by bubbling argon through the mixture. The phases were separated and the aqueous layer extracted with DCM. The combined organics were dried and concentrated to give a pale yellow oil (57 mg). This whole was dissolved in 1,2-DCE (5 ml) and added to N-(3-fluorophenyl)-4-piperidinamine hydrochloride (D4a) (78 mg, 0.341 mmol) and triethylamine (0.105 ml, 0.753 mmol). The mixture was heated to 140° C. in a microwave reactor for 5 minutes. PS-trisamine resin (0.2 g) was added and the mixture stirred for 10 minutes. The resin was removed by filtration and the filtrate concentrated to give the crude product as a yellow oil (227 mg). Column chromatography eluting with 0-60% EtOAc/petroleum ether gave the title compound as a colourless oil (67 mg). $\delta_H$ (CDCl$_3$, 400 MHz) 7.29 (2H, d), 7.04 (3H, m), 6.32 (2H, m), 6.21 (1H, m), 4.18 (1H, br s), 3.80 (3H, m), 3.60 (1H, m), 3.49 (1H, d), 3.37 (1H, d), 3.28 (1H, m), 3.21 (3H, s), 3.10 (1H, td), 2.75 (3H, m), 2.56 (1H, d), 2.12 (1H, dd), 2.01 (1H, td), 1.87 (2H, m), 1.47 (9H, s), 1.23 (3H, d), 1.17 (2H, m). MS (ES): MH$^+$ 540.

Description 33

Alternative Method (A)

1,1-Dimethylethyl (2S)-4-({4-[({4-[(3-fluorophenyl)amino]-1-piperidinyl}carbonyl)(methyl)amino]phenyl}methyl)-2-methyl-1-piperazinecarboxylate (D33)

To 1,1-dimethylethyl (2S)-2-methyl-4-{[4-(methylamino)phenyl]methyl}-1-piperazinecarboxylate (D23) (4.255 g, 13.319 mmol) in dry DCM (100 mL) was added saturated aqueous NaHCO$_3$ solution (100 mL) and the mixture was vigorously stirred with cooling in an ice bath for 10 min. The layers were allowed to separate then phosgene solution in toluene (20%, 1.85 M, 12.813 mL, 24.216 mmol) was added directly to the organic layer. The mixture was stirred vigorously for 10 min, then the organic phase was separated and the aqueous layer extracted twice with DCM. The combined organic extracts were dried and concentrated to give a white solid. This material was dissolved in 1,2-dichloroethane (80 mL) and N-(3-fluorophenyl)-4-piperidinamine (D4) (2.352 g, 12.108 mmol) was added, followed by triethylamine (1.685 mL, 12.108 mmol). The reaction mixture was heated at reflux for 2 h, then was allowed to cool to room temperature and was left to stand overnight under argon. The mixture was then treated with PS-trisamine resin (4.16 g) and stirred for 30 min at room temperature. The polymer was removed by filtration and the filtrate concentrated to give the crude product as a yellow gum (10.375 g). This material was combined with the crude product (10.499 g) obtained from a second preparation carried out on the same scale in parallel. The combined crude products were purified by column chromatography eluting with 0-80% EtOAc/petroleum ether to give the title compound as a cream foamy gum (8.281 g). Mass spectral and $^1$H NMR spectroscopic data consistent with those previously obtained for the product from Description 33.

The following intermediates, D34-D47, were prepared from the appropriate aniline and piperidine intermediates as indicated in the table using methods similar to that described for Description 33 in Description 33.

Compounds possess the general structure:

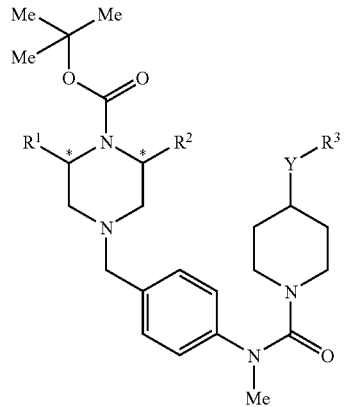

Where R$^1$, R$^2$ and YR$^3$ are exemplified in the table below

| | Intermediates | | | | | | |
|---|---|---|---|---|---|---|---|
| Description | Aniline | Piperidine | Compound | R$^1$ | R$^2$ | YR$^3$ | MH$^+$ |
| D34 | D23 | D2 | 1,1-dimethylethyl (2S)-4-({4-[({4-[(4-fluorophenyl)amino]-1-piperidinyl}carbonyl)(methyl)amino]phenyl}methyl)-2-methyl-1-piperazinecarboxylate | H | (S)-Me | ⌇NH–C$_6$H$_4$–F (para) | 540 |
| D35 | D23 | D6 | 1,1-dimethylethyl (2S)-4-({4-[({4-[(3-cyanophenyl)amino]-1-piperidinyl}carbonyl)(methyl)amino]phenyl}methyl)-2-methyl-1-piperazinecarboxylate | H | (S)-Me | ⌇NH–C$_6$H$_4$–CN (meta) | 547 |

-continued

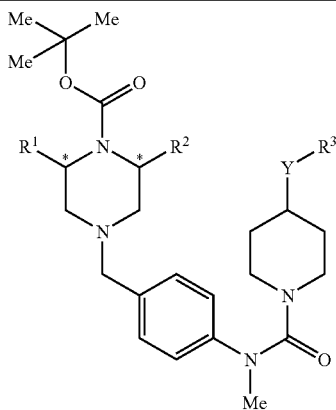

Where $R^1$, $R^2$ and $YR^3$ are exemplified in the table below

| | Intermediates | | | | | | |
|---|---|---|---|---|---|---|---|
| Description | Aniline | Piperidine | Compound | $R^1$ | $R^2$ | $YR^3$ | $MH^+$ |
| D36 | D23 | D16 | 1,1-dimethylethyl (2S)-4-({4-[({4-[(2-fluorophenyl)amino]-1-piperidinyl}carbonyl)(methyl)amino]phenyl}methyl)-2-methyl-1-piperazinecarboxylate | H | (S)-Me | 2-F-C6H4-NH- | 540 |
| D37 | D23 | D8 | 1,1-dimethylethyl (2S)-4-({4-[({4-[(4-cyanophenyl)amino]-1-piperidinyl}carbonyl)(methyl)amino]phenyl}methyl)-2-methyl-1-piperazinecarboxylate | H | (S)-Me | 4-CN-C6H4-NH- | 547 |
| D38 | D23 | D20 | 1,1-dimethylethyl (2S)-4-({4-[[(4-{[2-(aminocarbonyl)phenyl]amino}-1-piperidinyl)carbonyl](methyl)amino]phenyl}methyl)-2-methyl-1-piperazinecarboxylate | H | (S)-Me | 2-CONH2-C6H4-NH- | 565 |
| D39 | D23 | D12 | 1,1-dimethylethyl (2S)-4-({4-[({4-[(3-fluorophenyl)oxy]-1-piperidinyl}carbonyl)(methyl)amino]phenyl}methyl)-2-methyl-1-piperazinecarboxylate | H | (S)-Me | 3-F-C6H4-O- | 541 |
| D40 | D23 | D18 | 1,1-dimethylethyl (2S)-4-({4-[({4-[(2-cyanophenyl)amino]-1-piperidinyl}carbonyl)(methyl)amino]phenyl}methyl)-2-methyl-1-piperazinecarboxylate | H | (S)-Me | 2-CN-C6H4-NH- | 547 |
| D41 | D23 | D14 | 1,1-dimethylethyl (2S)-4-({4-[[(4-{[3-fluoro-4-(methyloxy)phenyl]amino}-1-piperidinyl)carbonyl](methyl)amino]phenyl}methyl)-2-methyl-1-piperazinecarboxylate | H | (S)-Me | 3-F-4-OMe-C6H3-NH- | 570 |

-continued

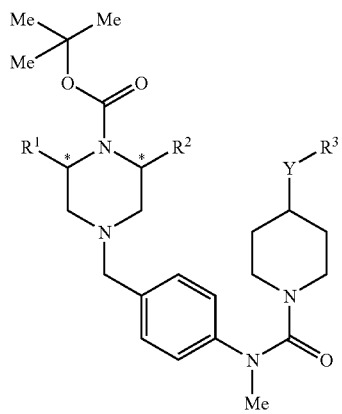

Where $R^1$, $R^2$ and $YR^3$ are exemplified in the table below

| | Intermediates | | | | | | |
|---|---|---|---|---|---|---|---|
| Description | Aniline | Piperidine | Compound | $R^1$ | $R^2$ | $YR^3$ | $MH^+$ |
| D42 | D23 | D10 | 1,1-dimethylethyl (2S)-4-({4-[[(4-{[4-fluoro-3-(methyloxy)phenyl]amino}-1-piperidinyl)carbonyl](methyl)amino]phenyl}methyl)-2-methyl-1-piperazinecarboxylate | H | (S)-Me | 4-F, 3-OMe anilino | 570 |
| D43 | D26 | D4 | 1,1-dimethylethyl (2R)-4-({4-[({4-[(3-fluorophenyl)amino]-1-piperidinyl}carbonyl)(methyl)amino]phenyl}methyl)-2-methyl-1-piperazinecarboxylate | H | (R)-Me | 3-F anilino | 540 |
| D44 | D29 | D4 | 1,1-dimethylethyl (2R,6S)-4-({4-[({4-[(3-fluorophenyl)amino]-1-piperidinyl}carbonyl)(methyl)amino]phenyl}methyl)-2,6-dimethyl-1-piperazinecarboxylate | (R)-Me | (S)-Me | 3-F anilino | 554 |
| D45 | D32 | D6 | 1,1-dimethylethyl 4-({4-[({4-[(3-cyanophenyl)amino]-1-piperidinyl}carbonyl)(methyl)amino]phenyl}methyl)-1-piperazinecarboxylate | H | H | 3-CN anilino | 533 |
| D46 | D32 | D4 | 1,1-dimethylethyl 4-({4-[({4-[(3-fluorophenyl)amino]-1-piperidinyl}carbonyl)(methyl)amino]phenyl}methyl)-1-piperazinecarboxylate | H | H | 3-F anilino | 526 |
| D47 | D32 | D2 | 1,1-dimethylethyl 4-({4-[({4-[(4-fluorophenyl)amino]-1-piperidinyl}carbonyl)(methyl)amino]phenyl}methyl)-1-piperazinecarboxylate | H | H | 4-F anilino | 526 |

Description 48

1,1-Dimethylethyl (2S)-4-({4-[{[4-(4-fluorophenyl)-1-piperidinyl]carbonyl}(methyl)amino]phenyl}methyl)-2-methyl-1-piperazinecarboxylate (D48)

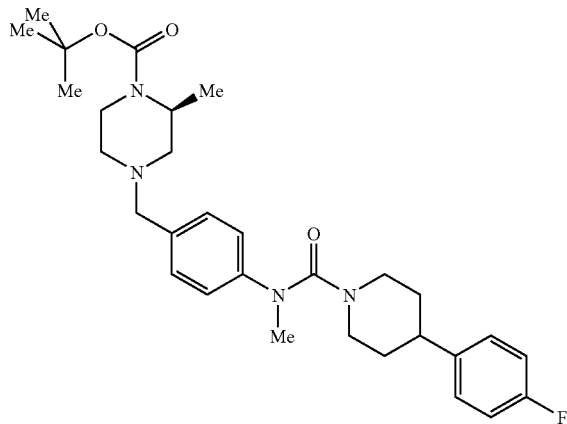

To a solution of 1,1-dimethylethyl (2S)-2-methyl-4-{[4-(methylamino)phenyl]methyl}-1-piperazinecarboxylate (D23) (100 mg, 0.31 mmol) in DCM (5 ml) was added saturated aqueous NaHCO$_3$ solution (5 ml) and the mixture stirred vigorously for 10 min at 0° C. The mixture was allowed to stand and a solution of phosgene in toluene (0.327 ml, 20% in toluene, 0.63 mmol) was injected into the DCM layer of the reaction mixture. The mixture was stirred for a further 10 min and the DCM layer was separated and the aqueous extracted with DCM. The combined organics were dried and concentrated to give a colourless oil. This whole was dissolved in 1,2-DCE (5 ml) and 4-(4-fluorophenyl)piperidine hydrochloride (74 mg, 0.34 mmol) and triethylamine (0.083 ml, 0.63 mmol) were added. The mixture was heated to 120° C. in a microwave reactor for 30 minutes. The reaction mixture was diluted with DCM/water and the organic layer separated, dried (Na$_2$SO$_4$) and concentration gave a crude colourless oil (189 mg). Column chromatography eluting with 0-10% EtOAc/petrol gave the title compound as a colourless oil (156 mg), MS (ES): MH$^+$ 525.3.

Description 49

1,1-Dimethylethyl (2S)-4-({4-[{[4-(3-fluorophenyl)-1-piperidinyl]carbonyl}(methyl)amino]phenyl}methyl)-2-methyl-1-piperazinecarboxylate (D49)

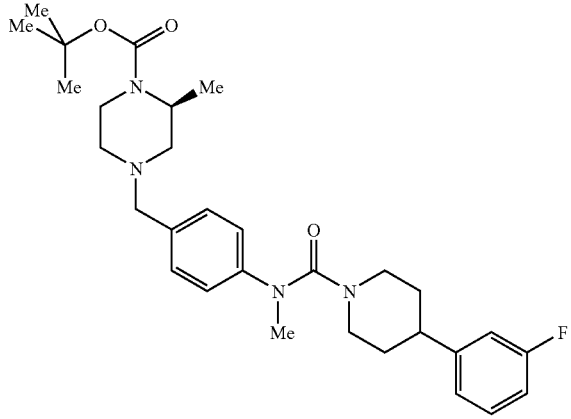

The title compound was prepared from 1,1-dimethylethyl (2S)-2-methyl-4-{[4-(methylamino)phenyl]methyl}-1-piperazinecarboxylate (D23) and 4-(3-fluorophenyl)piperidine using a method similar to that described for D48 in Description 48. MS (ES): MH$^+$ 525.2.

Description 50

1,1-Dimethylethyl (2S)-4-({4-[{[4-(3-cyanophenyl)-1-piperidinyl]carbonyl}(methyl)amino]phenyl}methyl)-2-methyl-1-piperazinecarboxylate (D50)

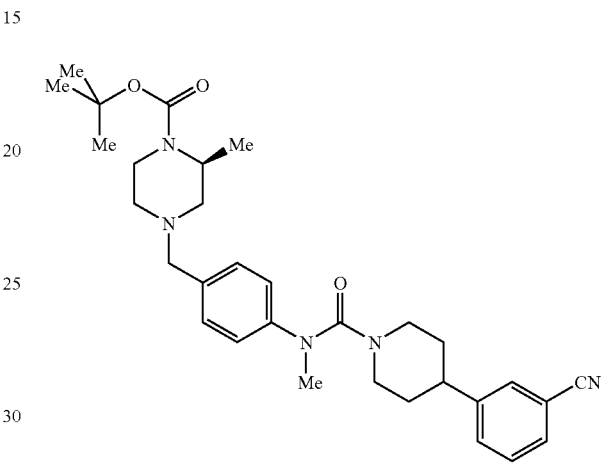

The title compound was prepared from 1,1-dimethylethyl (2S)-2-methyl-4-{[4-(methylamino)phenyl]methyl}-1-piperazinecarboxylate (D23) and 4-(3-cyanophenyl)piperidine using a method similar to that described for D48 in Description 48. MS (ES): MH$^+$ 532.4.

Description 51

N-[4-(Hydroxymethyl)-3-methylphenyl]acetamide (D51)

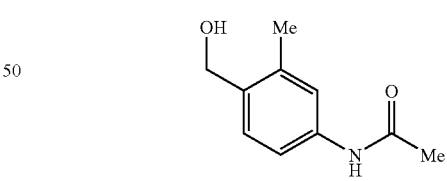

4-(Acetylamino)-2-methylbenzoic acid (2 g, 10.4 mmol) was suspended in THF (50 ml) and borane-THF complex (1M in THF, 26 ml, 26 mmol) added drop-wise over 15 minutes. The reaction mixture was stirred under argon at room temperature overnight then quenched with water (52 ml) and extracted with EtOAc (×3). The combined organics were dried and concentrated to give the crude product which was purified by column chromatography. Elution with 0-100% EtOAc/petroleum ether yielded the title compound as a cream solid (0.379 g). δ$_H$ (CD$_3$OD, 400 MHz) 7.36 (2H, d), 7.25 (1H, d), 4.57 (2H, s), 2.31 (3H, s), 2.10 (3H, s). MH$^+$ 180.2.

Description 52

N-(4-Formyl-3-methylphenyl)acetamide (D52)

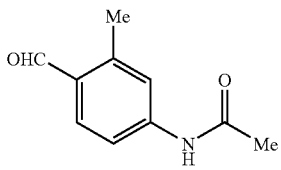

N-[4-(Hydroxymethyl)-3-methylphenyl]acetamide (D51) (0.36 g, 2 mmol) and manganese dioxide (0.875 g, 10 mmol) were combined in acetonitrile (16 ml) and heated to 120° C. in the microwave for 7 minutes. The MnO$_2$ was filtered off and the reaction mixture was concentrated to give the crude product which was purified by column chromatography. Elution with 0-100% EtOAc/petroleum ether yielded the title compound as a cream solid (0.326 g). δ$_H$ (CDCl$_3$, 400 MHz) 10.27 (1H, s), 7.79 (1H, d), 7.50 (1H, d), 7.45 (1H, s), 7.35 (1H, br.s), 2.66 (3H, s), 2.20 (3H, s). MH$^+$ 178.2.

Description 53

1,1-Dimethylethyl (2S)-4-{[4-(acetylamino)-2-methylphenyl]methyl}-2-methyl-1-piperazinecarboxylate (D53)

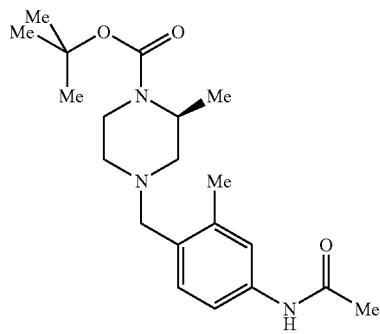

N-(4-Formyl-3-methylphenyl)acetamide (D52) (326 mg, 1.8 mmol), 1,1-dimethylethyl (2S)-2-methyl-1-piperazinecarboxylate hydrochloride (436 mg, 1.8 mmol), triethylamine (0.282 ml, 2 mmol) and sodium tri(acetoxy)borohydride (781 mg, 3.7 mmol) were stirred together in 1,2-DCE (15 ml) for 17 h. Saturated aqueous NaHCO$_3$ was added and the reaction mixture stirred for 1 h. The organic layer was separated and washed with water and brine, then dried and concentrated to give the crude product which was purified by chromatography. Elution with 0-100% EtOAc/petroleum ether yielded the title compound as a colourless oil (573 mg). δ$_H$ (CDCl$_3$, 400 MHz) 7.27 (2H, m), 7.16 (1H, d), 7.11 (1H, br.s), 4.17 (1H, m), 3.78 (1H, m), 3.36 (2H, s), 3.02 (1H, m), 2.70 (1H, m), 2.56 (1H, m), 2.36 (3H, s), 2.17 (4H, m), 1.95 (1H, m), 1.45 (9H, s), 1.18 (3H, d). MH$^+$ 362.3.

Description 54

1,1-Dimethylethyl (2S)-4-[(4-amino-2-methylphenyl)methyl]-2-methyl-1-piperazinecarboxylate (D54)

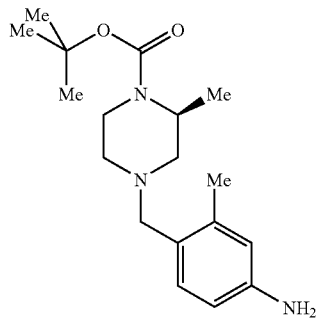

1,1-Dimethylethyl (2S)-4-{[4-(acetylamino)-2-methylphenyl]methyl}-2-methyl-1-piperazinecarboxylate (D53) (497 mg, 1.4 mmol) and KOH (1M aq. soln., 5 ml) were combined in MeOH (5 ml) and heated to 140° C. for 1 h in a microwave reactor. The reaction mixture was diluted with MeOH (5 ml) and heated for a total of 4 h 55 minutes at 130° C. in the microwave. The reaction mixture was concentrated to remove the MeOH and partitioned between DCM and water. The organic layer was dried and concentrated to give the crude product which was purified by column chromatography. Elution with 0-100% diethyl ether/petroleum ether followed by a column flush with 10% (2M NH$_3$ in MeOH) in DCM yielded the title compound as a yellow oil (233 mg). δ$_H$ (CDCl$_3$, 400 MHz) 6.97 (1H, d), 6.52 (1H, d), 6.46 (1H, dd), 4.17 (1H, br.s), 3.76 (1H, d), 3.57 (2H, br.s), 3.29 (2H, m), 3.01 (1H, td), 2.70 (1H, d), 2.56 (1H, d), 2.30 (3H, s), 2.10 (1H, dd), 1.90 (1H, m), 1.45 (9H, s), 1.18 (3H, d). MS (AP+): 342.3 (MNa$^+$), no molecular (MH$^+$) ion observed.

Description 55

1,1-Dimethylethyl (2S)-2-methyl-4-{[2-methyl-4-(methylamino)phenyl]methyl}-1-piperazinecarboxylate (D55)

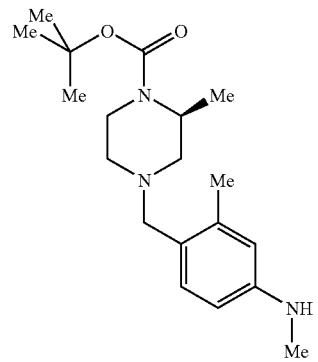

The title compound was prepared from 1,1-dimethylethyl (2S)-4-[(4-amino-2-methylphenyl)methyl]-2-methyl-1-piperazinecarboxylate (D54) using a method similar to that described for D23 in Description 23A although the reaction was heated at 50° C. for 16 h prior to addition of sodium borohydride and 5.5 h after addition. $\delta_H$ (CDCl$_3$, 400 MHz) 7.00 (1H, d), 6.45 (1H, d), 6.39 (1H, dd), 4.17 (1H, br.s), 3.76 (1H, d), 3.57 (1H, br.s), 3.33 (1H, d), 3.27 (1H, d), 3.01 (1H, td), 2.82 (3H, s), 2.71 (1H, d), 2.58 (1H, d), 2.32 (3H, s), 2.11 (1H, dd), 1.90 (1H, m), 1.45 (9H, s), 1.17 (3H, d). MS (AP$^+$): 356.2 (MNa$^+$), 234.2, no molecular ion (MH$^+$) observed.

Description 56

1,1-Dimethylethyl (2S)-4-({4-[({4-[(3-fluorophenyl) amino]-1-piperidinyl}carbonyl)(methyl)amino]-2-methylphenyl}methyl)-2-methyl-1-piperazinecarboxylate (D56)

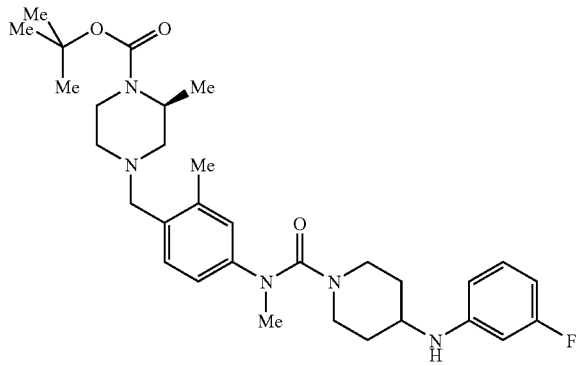

The title compound was prepared from 1,1-dimethylethyl (2S)-2-methyl-4-{[2-methyl-4-(methylamino)phenyl]methyl}-1-piperazinecarboxylate (D55) and N-(3-fluorophenyl)-4-piperidinamine (D4) using a method similar to that described for D48 in Description 48. MS (ES): MNa$^+$ 576.2, MH$^+$ 554.3.

Description 57

(3R,5S)-1-[(4-Nitrophenyl)methyl]-3,5-dimethylpiperazine (D57)

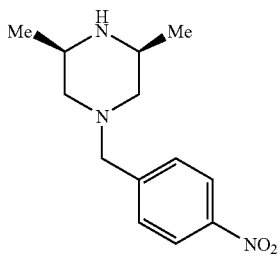

The title compound was prepared from 4-nitrobenzaldehyde and (2R,6S)-2,6-dimethylpiperazine using a method similar to that described for D21 in Description 21A. MS (ES): MH$^+$ 250.2.

Description 58

1,1-Dimethylethyl methylcarbamate (D58)

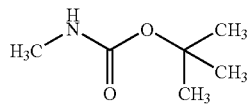

To a solution of Boc anhydride (7.5 g, 34.36 mmol) in DCM (40 mL) was added methylamine (173 mL, 2M solution in THF, 345 mmol) and the reaction mixture was stirred at room temperature overnight. The solvent and excess methylamine were removed in vacuo and dilute 2M HCl (10 mL) was added. The aqueous layer was extracted with DCM (×2) and the combined organics were dried and concentrated to give the title compound as a yellow oil (3.791 g). $\delta_H$ (CDCl$_3$, 400 MHz) 4.58 (1H, br.s), 2.73 (3H, d), 1.44 (9H, s).

Description 59

1,1-Dimethylethyl (6-formyl-3-pyridinyl)methylcarbamate (D59)

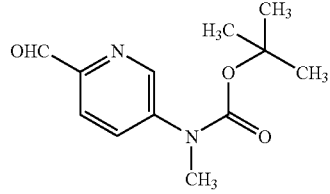

A mixture of 5-bromo-2-pyridinecarbaldehyde (1.5 g, 8.064 mmol), 1,1-dimethylethyl methylcarbamate (D58) (1.267 g, 9.677 mmol), tris(dibenzylideneacetone) dipalladium(0) (0.148 g, 0.161 mmol), xantphos (0.373 g, 0.645 mmol) and cesium carbonate (3.678 g, 11.289 mmol) in dioxane (35 mL) was heated at 110° C. overnight under an argon atmosphere. On cooling, the solvent was removed in vacuo and the residue partitioned between EtOAc and water. The organic layer was separated, washed with water and brine, dried and concentrated to give the crude product which was purified by column chromatography. Elution with 0-50% ether/petroleum ether gave the title compound as a brown oil (0.977 g). $\delta_H$ (CDCl$_3$, 400 MHz) 10.01 (1H, s), 8.79 (1H, d), 7.94 (1H, d), 7.86 (1H, dd), 3.40 (3H, s), 1.53 (9H, s). MS (ES): 259.1 (MNa$^+$), 181.2, no molecular ion (MH$^+$) observed.

Description 60

5-(Methylamino)-2-pyridinecarbaldehyde and 6-[bis (methyloxy)methyl]-N-methyl-3-pyridinamine (D60)

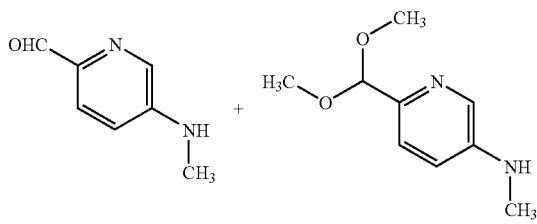

To a solution of 1,1-dimethylethyl (6-formyl-3-pyridinyl) methylcarbamate (D59) (0.977 g, 4.139 mmol) in DCM (80 mL) was added TFA (20 mL) and the reaction mixture was stirred at room temperature for 2 h. The solvent was removed in vacuo and the residue was taken up in methanol and eluted through an SCX (10 g) column with methanol then 2M NH$_3$ in methanol solution. The ammoniacal fraction was concentrated to give a yellow oil (0.622 g) which was an approximately 1:1 mixture of the title compounds, and was used directly in the next step. MS (ES+): aldehyde—137 (MH+); acetal—151. MS (AP+): aldehyde—137 (MH+); acetal—205 (MNa+), 151.

Description 61

1,1-Dimethylethyl (2S)-2-methyl-4-{[5-(methylamino)-2-pyridinyl]methyl}-1-piperazinecarboxylate (D61)

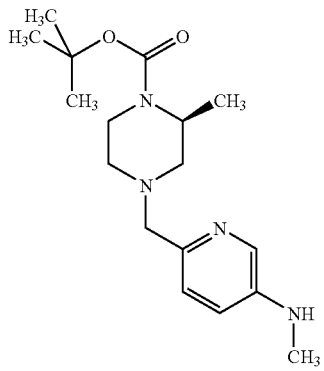

A mixture of 5-(methylamino)-2-pyridinecarbaldehyde and 6-[bis(methyloxy)methyl]-N-methyl-3-pyridinamine (D60) (0.622 g), 1,1-dimethylethyl (2S)-2-methyl-1-piperazinecarboxylate (0.910 g, 4.552 mmol) and triethylamine (0.418 g, 4.139 mmol) in 1,2-DCE (40 mL) was stirred at room temperature overnight. Sodium tri(acetoxy)borohydride (1.14 g, 5.38 mmol) was added and the reaction stirred at room temperature overnight. The reaction mixture was diluted with DCM and washed with saturated aq. NaHCO$_3$ solution and water. The organic layer was dried and concentrated to give the crude product which was purified by column chromatography. Elution with 0-100% EtOAc/petroleum ether gave the title compound as a yellow/brown oil (0.542 g). δ$_H$ (CDCl$_3$, 400 MHz) 7.96 (1H, d), 7.23 (1H, d), 6.88 (1H, dd), 4.17 (1H, br.s), 3.80 (2H, d), 3.58 (1H, d), 3.45 (1H, d), 3.12 (1H, td), 2.86 (3H, s), 2.76 (1H, m), 2.58 (1H, m), 2.18 (1H, dd), 2.07 (1H, m), 1.45 (9H, s), 1.23 (3H, d). MS (ES): MH+ 321.4

Description 62

1,1-Dimethylethyl (2S)-4-({5-[({4-[(3-fluorophenyl)amino]-1-piperidinyl}carbonyl)(methyl)amino]-2-pyridinyl}methyl)-2-methyl-1-piperazinecarboxylate (D62)

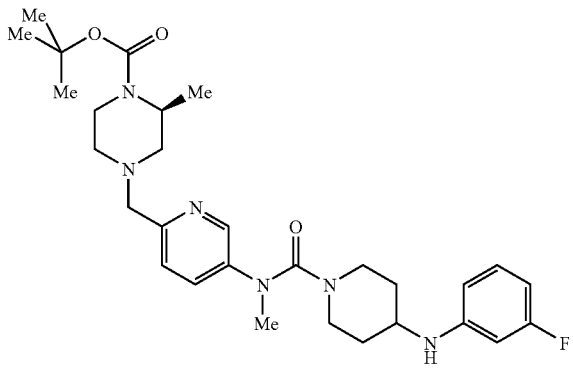

The title compound was prepared from 1,1-dimethylethyl (2S)-2-methyl-4-{[5-(methylamino)-2-pyridinyl]methyl}-1-piperazinecarboxylate (D61) and N-(3-fluorophenyl)-4-piperidinamine (D4) using a procedure similar to that described for D33 in Description 33A. MS (ES): MH+ 541.4.

EXAMPLE 1

4-[(3-Fluorophenyl)amino]-N-methyl-N-(4-{[(3S)-3-methyl-1-piperazinyl]methyl}phenyl)-1-piperidinecarboxamide (E1)

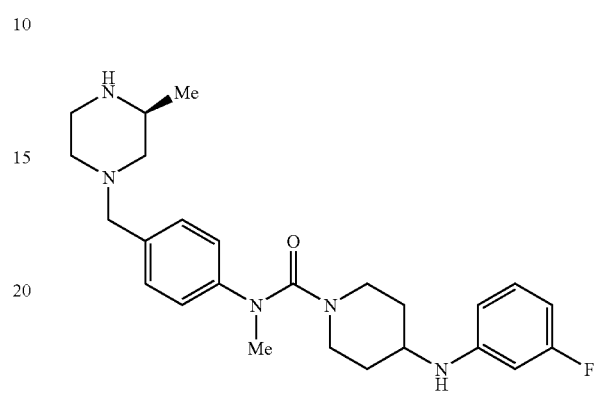

A solution of 1,1-dimethylethyl (2S)-4-({4-[({4-[(3-fluorophenyl)amino]-1-piperidinyl}carbonyl)(methyl)amino]phenyl}methyl)-2-methyl-1-piperazinecarboxylate (D33) (67 mg, 0.124 mmol) in DCM (2.5 ml) and TFA (0.5 ml) was stirred at room temp for ~1.5 h. The solvent was removed in vacuo and the residue partitioned between DCM and saturated aqueous NaHCO$_3$ solution. The aqueous layer was further extracted with DCM and the combined organic layers were dried and concentrated to give the crude product as a pale yellow oil. Column chromatography eluting with 0-10% (2M NH$_3$ in MeOH)/DCM gave the title compound as a pale yellow oil (44 mg). δ$_H$ (CDCl$_3$, 400 MHz) 7.27 (2H, d), 7.05 (3H, m), 6.34 (1H, m), 6.29 (1H, m), 6.21 (1H, m), 3.77 (2H, d), 3.62 (1H, d), 3.47 (2H, m), 3.38 (1H, m), 3.21 (3H, s), 2.93 (3H, m), 2.75 (3H, m), 2.20 (1H+H$_2$O, br. s), 2.05 (1H, td), 1.85 (2H, m), 1.72 (1H, m), 1.16 (2H, m), 1.04 (3H, d). MS (ES): MH+ 440.2.

This whole was dissolved in DCM and treated with 1M HCl in Et$_2$O (100 ul). The solvent was removed in vacuo to give the hydrochloride salt of the title compound as a white solid (47 mg). MS (ES): MH+ 440.2.

EXAMPLE 1

Alternative Method (A)

4-[(3-Fluorophenyl)amino]-N-methyl-N-(4-{[(3S)-3-methyl-1-piperazinyl]methyl}phenyl)-1-piperidinecarboxamide (E1)

1,1-Dimethylethyl (2S)-4-({4-[({4-[(3-fluorophenyl)amino]-1-piperidinyl}carbonyl)(methyl)amino]phenyl}methyl)-2-methyl-1-piperazinecarboxylate (D33) (9.337 g, 17.322 mmol) was dissolved in DCM (144 mL) and cooled in an ice bath. TFA (36 mL) was added slowly and the mixture was allowed to stir for 2.5 h under argon. The solvent was removed under vacuum and the residue partitioned between DCM and saturated aqueous NaHCO$_3$. The organic layer was separated and the aqueous layer extracted twice with DCM. The combined organic extracts were dried and concentrated to give the title compound as a cream coloured foam (7.82 g). MS (ES): MH+ 440.3.

A portion of this material (6.802 g) was taken up in EtOAc (200 mL), resulting in rapid crystallisation. The solvent was removed in vacuo and the crystalline residue was re-dissolved in DCM (100 mL) to give a pale yellow solution. Treatment with 1M HCl in Et$_2$O (15.49 mL) initially gave a precipitate which, on completion of the addition, formed a homogeneous solution. The solution was concentrated in vacuo to give a semi-solid, which was triturated with EtOAc (200 mL) and vigorously stirred overnight at room temperature. The resulting white granular precipitate was collected by filtration and washed with EtOAc then dried in vacuo at 40° C. for approximately 30 mins to give the hydrochloride salt of the title compound (4.27 g). $\delta_H$ (CD$_3$OD, 400 MHz) 7.55 (2H, d), 7.22 (2H, d), 7.16 (1H, dd), 6.62 (1H, d), 6.49-6.57 (2H, m), 4.19 (2H, s), 3.30 (2H, d), 3.69 (1H, m), 3.45 (4H, m), 3.59 (1H, m), 3.20 (3H, s), 3.10 (1H, m), 2.91 (1H, m), 2.83 (2H, t), 1.85 (2H, d), 1.35 (3H, d), 1.30 (2H, m).

The following examples, E2-E15, were prepared from the appropriate intermediate, as indicated in the table, using methods similar to that described for E1 in Example 1 with reaction times as indicated in the table.

Compounds possess the general structure:

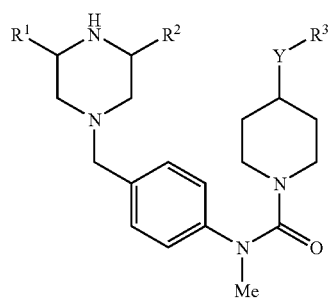

Where R$^1$, R$^2$ and YR$^3$ are exemplified in the table below

| Example | Intermediate | Reaction Time | Compound | R$^1$ | R$^2$ | YR$^3$ | MH$^+$ |
|---|---|---|---|---|---|---|---|
| E2 | D34 | 1 h | 4-[(4-fluorophenyl)amino]-N-methyl-N-(4-{[(3S)-3-methyl-1-piperazinyl]methyl}phenyl)-1-piperidinecarboxamide | H | (S)-Me | 4-F-C$_6$H$_4$-NH- | 440 |
| E3 | D35 | 1 h | 4-[(3-cyanophenyl)amino]-N-methyl-N-(4-{[(3S)-3-methyl-1-piperazinyl]methyl}phenyl)-1-piperidinecarboxamide | H | (S)-Me | 3-CN-C$_6$H$_4$-NH- | 447 |
| E4 | D36 | 1.5 h | 4-[(2-fluorophenyl)amino]-N-methyl-N-(4-{[(3S)-3-methyl-1-piperazinyl]methyl}phenyl)-1-piperidinecarboxamide | H | (S)-Me | 2-F-C$_6$H$_4$-NH- | 440 |
| E5 | D37 | 3 h | 4-[(4-cyanophenyl)amino]-N-methyl-N-(4-{[(3S)-3-methyl-1-piperazinyl]methyl}phenyl)-1-piperidinecarboxamide | H | (S)-Me | 4-CN-C$_6$H$_4$-NH- | 447 |
| E6 | D38 | 2 h | 4-{[2-(aminocarbonyl)phenyl]amino}-N-methyl-N-(4-{[(3S)-3-methyl-1-piperazinyl]methyl}phenyl)-1-piperidinecarboxamide | H | (S)-Me | 2-CONH$_2$-C$_6$H$_4$-NH- | 465 |
| E7 | D39 | 2 h | 4-[(3-fluorophenyl)oxy]-N-methyl-N-(4-{[(3S)-3-methyl-1-piperazinyl]methyl}phenyl)-1-piperidinecarboxamide | H | (S)-Me | 3-F-C$_6$H$_4$-O- | 441 |

-continued

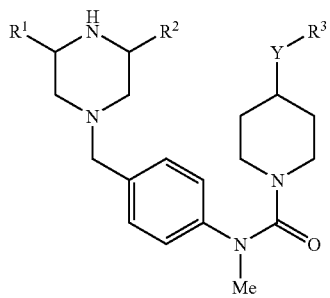

Where R¹, R² and YR³ are exemplified in the table below

| Example | Intermediate | Reaction Time | Compound | R¹ | R² | YR³ | MH⁺ |
|---|---|---|---|---|---|---|---|
| E8 | D40 | 2 h | 4-[(2-cyanophenyl)amino]-N-methyl-N-(4-{[(3S)-3-methyl-1-piperazinyl]methyl}phenyl)-1-piperidinecarboxamide | H | (S)-Me | 2-CN-C₆H₄-NH- | 447 |
| E9 | D41 | 2 h | 4-{[3-fluoro-4-(methyloxy)phenyl]amino}-N-methyl-N-(4-{[(3S)-3-methyl-1-piperazinyl]methyl}phenyl)-1-piperidinecarboxamide | H | (S)-Me | 3-F-4-OMe-C₆H₃-NH- | 470 |
| E10 | D42 | 2 h | 4-{[4-fluoro-3-(methyloxy)phenyl]amino}-N-methyl-N-(4-{[(3S)-3-methyl-1-piperazinyl]methyl}phenyl)-1-piperidinecarboxamide | H | (S)-Me | 4-F-3-OMe-C₆H₃-NH- | 470 |
| E11 | D43 | 2 h | 4-[(3-fluorophenyl)amino]-N-methyl-N-(4-{[(3R)-3-methyl-1-piperazinyl]methyl}phenyl)-1-piperidinecarboxamide | H | (R)-Me | 3-F-C₆H₄-NH- | 440 |
| E12 | D44 | 1.5 h | N-(4-{[(3R,5S)-3,5-dimethyl-1-piperazinyl]methyl}phenyl)-4-[(3-fluorophenyl)amino]-N-methyl-1-piperidinecarboxamide | (R)-Me | (S)-Me | 3-F-C₆H₄-NH- | 454 |
| E13 | D45 | 3 h | 4-[(3-cyanophenyl)amino]-N-methyl-N-[4-(1-piperazinylmethyl)phenyl]-1-piperidinecarboxamide | H | H | 3-CN-C₆H₄-NH- | 433 |
| E14 | D46 | 3.5 h | 4-[(3-fluorophenyl)amino]-N-methyl-N-[4-(1-piperazinylmethyl)phenyl]-1-piperidinecarboxamide | H | H | 3-F-C₆H₄-NH- | 426 |
| E15 | D47 | 3.5 h | 4-[(4-fluorophenyl)amino]-N-methyl-N-[4-(1-piperazinylmethyl)phenyl]-1-piperidinecarboxamide | H | H | 4-F-C₆H₄-NH- | 426 |

EXAMPLE 16

4-(4-Fluorophenyl)-N-methyl-N-(4-{[(3S)-3-methyl-1-piperazinyl]methyl}phenyl)-1-piperidinecarboxamide (E16)

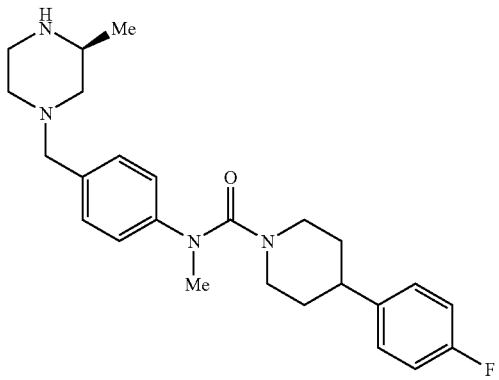

A solution of 1,1-dimethylethyl (2S)-4-({4-[{[4-(4-fluorophenyl)-1-piperidinyl]carbonyl}(methyl)amino]phenyl}methyl)-2-methyl-1-piperazinecarboxylate (D48) (156 mg, 0.3 mmol) in dry DCM (20 ml) and TFA (5 ml) was stirred at room temp under argon for 5 h. The reaction mixture was concentrated and diluted with DCM/water. The aqueous layer was separated and basified to pH14 with conc NaOH, extracted with DCM (×3), dried (Na$_2$SO$_4$) and concentration gave a colourless oil (111 mg). Column chromatography eluting with 0-10% (MeOH/NH$_3$ in DCM)/DCM gave the title compound as a colourless oil (92 mg). δ$_H$ (CDCl$_3$, 400 MHz) 7.29 (2H, d), 7.06 (4H, m), 6.95 (2H, m), 3.95 (2H, m), 3.46 (2H, s), 3.23 (3H, s), 2.82-2.97 (3H, m), 2.74 (2H, d), 2.65 (2H, m), 2.52 (1H, m), 2.02 (1H, td), 1.69 (1H, m), 1.82 (1H+H$_2$O, br.s), 1.62 (2H, d), 1.40 (2H, m), 0.98 (3H, d). MS (ES): MH$^+$ 425.2.

This whole was dissolved in MeOH and treated with 1M HCl in Et$_2$O (0.24 ml) to give the hydrochloride salt of the title compound as a pale yellow oil (92.5 mg), MS (ES): MH$^+$ 425.3.

EXAMPLE 17

4-(3-Fluorophenyl)-N-methyl-N-(4-{[(3S)-3-methyl-1-piperazinyl]methyl}phenyl)-1-piperidinecarboxamide (E17)

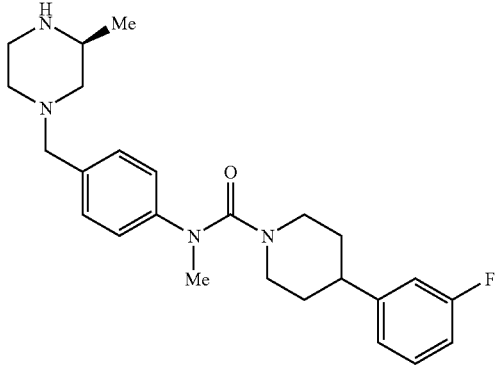

The title compound was prepared from 1,1-dimethylethyl (2S)-4-({4-[{[4-(3-fluorophenyl)-1-piperidinyl]carbonyl}(methyl)amino]phenyl}methyl)-2-methyl-1-piperazinecarboxylate (D49) using a method similar to that described for E16 in Example 16. MS (ES): MH$^+$ 425.2.

EXAMPLE 18

4-(3-Cyanophenyl)-N-methyl-N-(4-{[(3S)-3-methyl-1-piperazinyl]methyl}phenyl)-1-piperidinecarboxamide (E18)

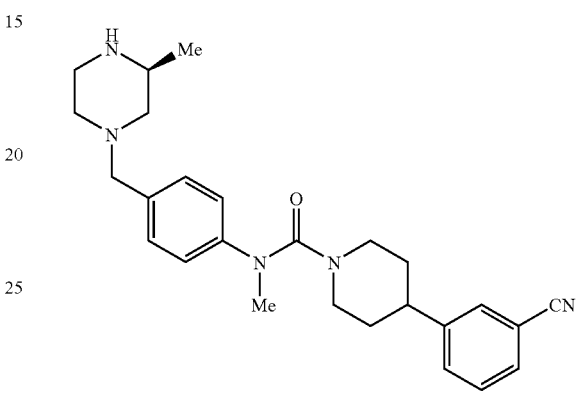

The title compound was prepared from 1,1-dimethylethyl (2S)-4-({4-[{[4-(3-cyanophenyl)-1-piperidinyl]carbonyl}(methyl)amino]phenyl}methyl)-2-methyl-1-piperazinecarboxylate (D50) using a method similar to that described for E16 in Example 16. MS (ES): MH$^+$ 432.1.

EXAMPLE 19

4-[(3-Fluorophenyl)amino]-N-methyl-N-(3-methyl-4-{[(3S)-3-methyl-1-piperazinyl]methyl}phenyl)-1-piperidinecarboxamide (E19)

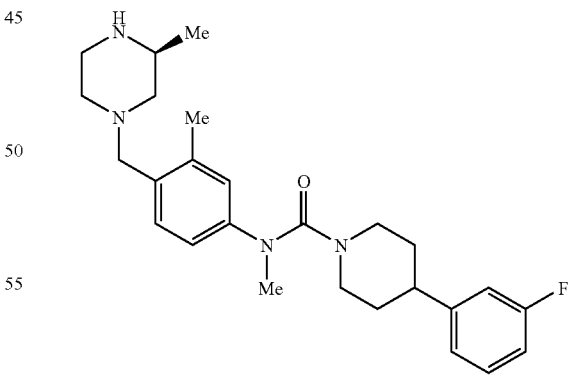

The title compound was prepared from 1,1-dimethylethyl (2S)-4-({4-[({4-[(3-fluorophenyl)amino]-1-piperidinyl}carbonyl)(methyl)amino]-2-methylphenyl}methyl)-2-methyl-1-piperazinecarboxylate (D56) using a method similar to that described for E16 in Example 16, except that chromatography was carried out using Biotage KP-NH™ column eluting with 0-100% EtOAc/petrol. MS (ES): MH$^+$ 454.3.

EXAMPLE 20

4-[(3-Fluorophenyl)amino]-N-methyl-N-(6-{[(3S)-3-methyl-1-piperazinyl]methyl}-3-pyridinyl)-1-piperidinecarboxamide (E20)

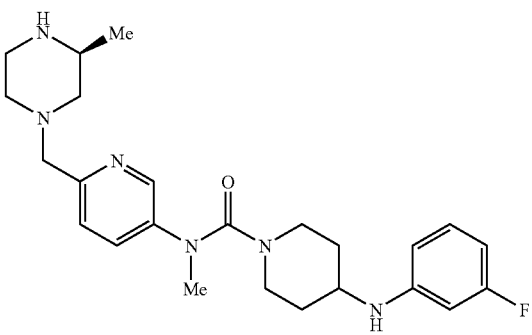

A solution of 1,1-dimethylethyl (2S)-4-({5-[({4-[(3-fluorophenyl)amino]-1-piperidinyl}carbonyl)(methyl)amino]-2-pyridinyl}methyl)-2-methyl-1-piperazinecarboxylate (D62) (320 mg, 0.593 mmol) in DCM (16 ml) and TFA (4 ml) was stirred at room temp for 2 h. The solvent was removed in vacuo and the residue was taken up in MeOH, and loaded onto an Isolute SCX cartridge which was eluted with MeOH then 2M $NH_3$ in MeOH. The ammoniacal fraction was concentrated to give the crude product as a yellow oil. Column chromatography eluting with 0-10% (2M $NH_3$ in MeOH)/DCM gave the title compound as a pale yellow oil (240 mg). MS (ES) $MH^+$ 441.3.

This whole was dissolved in DCM and treated with 1M HCl in $Et_2O$ (545 ul). The solvent was removed in vacuo to give the hydrochloride salt of the title compound as a white solid (261 mg). MS (ES): $MH^+$ 441.3.

The following tabulated examples E21-E22 were prepared using methods similar to that described for Examples E1.

| Example No. | Structure | Name | MH+ |
|---|---|---|---|
| E21 | 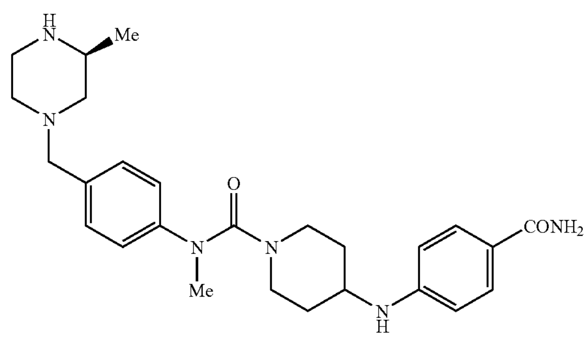 | 4-{[4-(aminocarbonyl)phenyl]amino}-N-methyl-N-(4-{[(3S)-3-methyl-1-piperazinyl]methyl}phenyl)-1-piperidinecarboxamide | 465.2 |
| E22 | 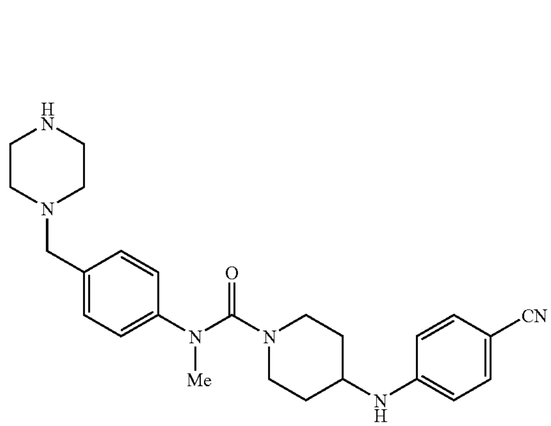 | 4-[(4-cyanophenyl)amino]-N-methyl-N-[4-(1-piperazinylmethyl)phenyl]-1-piperidinecarboxamide | 433.1 |

GPR38 FLIPR Functional Agonist Assay Protocol 24 hours prior to assay, CHO-K1 cells stably expressing the GPR38 receptor were seeded (10,000 cells/well) into poly-D-lysine coated 384-well black-wall, clear-bottom microtitre plates (Greiner). On the day of assay, media was aspirated from cell plates using a cell washer (leaving 10 ul of media). Cells were immediately loaded with loading buffer [Tyrodes (Elga water+145 mM NaCl+5 mM KCl+20 mM HEPES+10 mM glucose+1 mM $MgCl_2$)+1.5 mM $CaCl_2$+ 0.714 mg/ml Probenicid (predissolved in 1 M NaOH)+0.25 mM brilliant black+2 uM Fluo 4 dye], and incubated at 37.5° C. for 1 hour.

Plates were then assayed on a FLuorometric Imaging Plate Reader (FLIPR, Molecular Devices).

Master compound plates were prepared in 100% DMSO. A top concentration of 3 mM was used (giving 12 μM final concentration in assay) and this was serially diluted 1 in 4. 1 ul from the master plate was transferred to a daughter plate, to which 50 μl of compound dilution buffer (Tyrodes+1 mg/ml BSA+1.5 mM $CaCl_2$) was added. In the FLIPR, 10 ul of test compound was added to the cells and changes in fluorescence measured over a 1 minute timeframe. Maximum change in fluorescence over baseline was used to determine agonist response and concentration response curves were constructed, using a 4-parameter logistic equation.

In alternative protocols the loading buffer was HBSS {Elga water+137 mM NaCl+5 mM KCl+0.41 mMa KH2PO4(anhyd)+20 mM HEPES+5 mM glucose+0.81 mM MgSO4(anhyd)+1.3 mM CaCl2+4.16 mM NaHCO3}+0.25 mM brilliant black+2 uM Fluo 4 dye and the CHO-K1 cells thawed from frozen aliquots and seeded 24 hours prior to the assay.

Examples 1 to 20 have a pEC50 ≧6.4 in the FLIPR assay.

The invention claimed is:
1. A compound of formula (I):

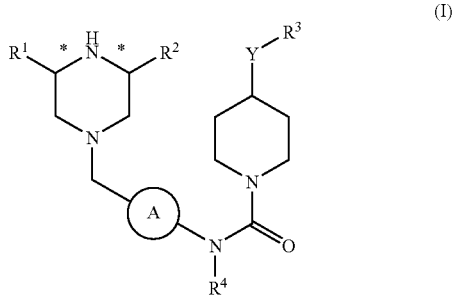

wherein:
A is phenyl or pyridyl, optionally substituted with halogen, $C_{(1-4)}$alkyl or $C_{(1-4)}$alkoxy;
$R^1$ and $R^2$ are independently H or $C_{(1-4)}$ alkyl;
$R^3$ is an optionally substituted phenyl, wherein when $R^3$ is a substituted phenyl, said substituted phenyl has 1, 2 or 3 substituents, each independently selected from halogen, $C_{(1-4)}$alkyl, $C_{(1-4)}$alkoxy, $C_{(3-7)}$cycloalkyl, hydroxy, trifluoromethoxy, trifluoromethyl, nitro, cyano, phenyl, $NH_2$, $NHR^5$, $NR^5R^6$, $NHCOR^5$, $NHSO_2R^5$, $C(O)CF_3$, $C(O)C_{(1-4)}$alkyl, $C(O)C_{(3-7)}$cycloalkyl, $C(O)OC_{(1-4)}$alkyl, $C(O)OC_{(3-7)}$cycloalkyl, $OC(O)C_{(1-4)}$alkyl, $OC(O)C_{(3-7)}$cycloalkyl, $CONH_2$, $CONHR^5$, $CONR^5R^6$, $SOR^6$, $SO_2CF_3$, $SO_2R^6$, $OSO_2R^6$, $OSO_2CF_3$, $SO_2NH_2$, $SO_2NHR^5$ and $SO_2NR^5R^6$;
wherein $R^5$ and $R^6$ may be the same or different and are independently selected from $C_{(1-4)}$alkyl, phenyl optionally substituted with halogen, and 5 or 6 membered heteroaryl optionally substituted with halogen;
Y is NH, O, $CH_2$ or a bond; and
$R^4$ is $C_{(1-4)}$ alkyl or $C_{(1-4)}$ alkoxy $C_{(1-4)}$ alkyl;
or a salt thereof.

2. The compound or salt according to claim 1, wherein the (piperazinyl)methylene substituent and $—NR^4$ are para- to each other across ring A.

3. The compound or salt according to claim 1, wherein $R^1$ is hydrogen or methyl.

4. The compound or salt according to claim 1, wherein $R^2$ is hydrogen or methyl.

5. The compound or salt according to claim 1, wherein $R^3$ is substituted by one to two substituents selected from fluoro, cyano, aminocarbonyl and methoxy.

6. The compound or salt according to claim 1, wherein Y is NH, O or a bond.

7. The compound or salt according to claim 1, wherein Y is NH.

8. The compound or salt according to claim 1, wherein $R^4$ is methyl.

9. The compound or salt according to claim 1, wherein:
A is phenyl or pyridyl;
$R^1$ is hydrogen or methyl;
$R^2$ is hydrogen or methyl;
Y is NH, O or a bond; and
$R^4$ is methyl.

10. The salt according to claim 9, wherein said salt is a pharmaceutically acceptable salt.

11. A compound selected from the group consisting of:
4-[(3-fluorophenyl)amino]-N-methyl-N-(4-{[(3S)-3-methyl-1-piperazinyl]methyl}phenyl)-1-piperidinecarboxamide;
4-[(4-fluorophenyl)amino]-N-methyl-N-(4-{[(3S)-3-methyl-1-piperazinyl]methyl}phenyl)-1-piperidinecarboxamide;
4-[(3-cyanophenyl)amino]-N-methyl-N-(4-{[(3S)-3-methyl-1-piperazinyl]methyl}phenyl)-1-piperidinecarboxamide;
4-[(2-fluorophenyl)amino]-N-methyl-N-(4-{[(3S)-3-methyl-1-piperazinyl]methyl}phenyl)-1-piperidinecarboxamide;
4-[(4-cyanophenyl)amino]-N-methyl-N-(4-{[(3S)-3-methyl-1-piperazinyl]methyl}phenyl)-1-piperidinecarboxamide;
4-{[2-(aminocarbonyl)phenyl]amino}-N-methyl-N-(4-{[(3S)-3-methyl-1-piperazinyl]methyl}phenyl)-1-piperidinecarboxamide;
4-[(3-fluorophenyl)oxy]-N-methyl-N-(4-{[(3S)-3-methyl-1-piperazinyl]methyl}phenyl)-1-piperidinecarboxamide;
4-[(2-cyanophenyl)amino]-N-methyl-N-(4-{[(3S)-3-methyl-1-piperazinyl]methyl}phenyl)-1-piperidinecarboxamide;
4-{[3-fluoro-4-(methyloxy)phenyl]amino}-N-methyl-N-(4-{[(3S)-3-methyl-1-piperazinyl]methyl}phenyl)-1-piperidinecarboxamide;
4-{[4-fluoro-3-(methyloxy)phenyl]amino}-N-methyl-N-(4-{[(3S)-3-methyl-1-piperazinyl]methyl}phenyl)-1-piperidinecarboxamide;
4-[(3-fluorophenyl)amino]-N-methyl-N-(4-{[(3R)-3-methyl-1-piperazinyl]methyl}phenyl)-1-piperidinecarboxamide;
N-(4-{[(3R,5S)-3,5-dimethyl-1-piperazinyl]methyl}phenyl)-4-[(3-fluorophenyl)amino]-N-methyl-1-piperidinecarboxamide;

4-[(3-cyanophenyl)amino]-N-methyl-N-[4-(1-piperazinylmethyl)phenyl]-1-piperidinecarboxamide;
4-[(3-fluorophenyl)amino]-N-methyl-N-[4-(1-piperazinylmethyl)phenyl]-1-piperidinecarboxamide;
4-[(4-fluorophenyl)amino]-N-methyl-N-[4-(1-piperazinylmethyl)phenyl]-1-piperidinecarboxamide;
4-(4-fluorophenyl)-N-methyl-N-(4-{[(3S)-3-methyl-1-piperazinyl]methyl}phenyl)-1-piperidinecarboxamide;
4-(3-fluorophenyl)-N-methyl-N-(4-{[(3S)-3-methyl-1-piperazinyl]methyl}phenyl)-1-piperidinecarboxamide;
4-(3-cyanophenyl)-N-methyl-N-(4-{[(3S)-3-methyl-1-piperazinyl]methyl}phenyl)-1-piperidinecarboxamide;
4-[(3 --fluorophenyl)amino]-N-methyl-N-(4-{[(3S)-3-methyl-1-piperazinyl]methyl}phenyl)-1-piperidinecarboxamide;
4-[(3-fluorophenyl)amino]-N-methyl-N-(3-methyl-4-{[(3S)-3-methyl-1-piperazinyl]methyl}phenyl)-1-piperidinecarboxamide; and
4-[(3-fluorophenyl)amino]-N-methyl-N-(6-{[(3S)-3-methyl-1-piperazinyl]methyl}-3-pyridinyl)-1-piperidinecarboxamide;

or a pharmaceutically acceptable salt thereof.

12. A compound which is 4-[(3-fluorophenyl)amino]-N-methyl-N-(4-{[(3S)-3-methyl-1-piperazinyl]methyl}phenyl)-1-piperidinecarboxamide.

13. A pharmaceutical composition comprising the compound according to claim 1 or a pharmaceutically acceptable salt thereof and a pharmaceutically acceptable carrier.

14. A pharmaceutical composition comprising the compound or salt according to claim 12 and a pharmaceutically acceptable carrier.

15. A method of treating a gastroesophageal reflux disorder, which method comprises administering to a human in need thereof an effective amount of the compound or salt thereof according to claim 1.

16. A method of treating functional dyspepsia, which method comprises administering to a human in need thereof an effective amount of the compound or salt thereof according to claim 1.

17. A method of treating gastric stasis, which method comprises administering to a human in need thereof an effective amount of the compound or salt thereof according to claim 1.

18. A method of treating hypomotility in enterally fed patients, which method comprises administering to a human in need thereof an effective amount of the compound or salt thereof according to claim 1.

19. A method of treating a gastroesophageal reflux disorder, which method comprises administering to a human in need thereof an effective amount of the compound according to claim 12.

20. A method of treating functional dyspepsia, which method comprises administering to a human in need thereof an effective amount of the compound according to claim 12.

21. A method of treating gastric stasis, which method comprises administering to a human in need thereof an effective amount of the compound according to claim 12.

22. A method of treating hypomotility in enterally fed patients, which method comprises administering to a human in need thereof an effective amount of the compound according to claim 12.

* * * * *